US012805943B2

(12) United States Patent
Sorajja et al.

(10) Patent No.: US 12,805,943 B2
(45) Date of Patent: Nov. 24, 2026

(54) DEVICES AND METHODS FOR GUIDE WIRE PLACEMENT

(71) Applicant: Cultiv8 Medical, LLC, Minneapolis, MN (US)

(72) Inventors: Paul Sorajja, Plymouth, MN (US); Gorav Ailawadi, Plymouth, MN (US); Daniel P. Coyle, Plymouth, MN (US); Karl Alexander Kabarowski, Plymouth, MN (US)

(73) Assignee: Cultiv8 Medical, LLC, Minneapolis, MN (US)

( * ) Notice: Subject to any disclaimer, the term of this patent is extended or adjusted under 35 U.S.C. 154(b) by 160 days.

(21) Appl. No.: 18/673,863

(22) Filed: May 24, 2024

(65) Prior Publication Data

US 2024/0307128 A1 Sep. 19, 2024

Related U.S. Application Data

(63) Continuation of application No. 17/597,883, filed as application No. PCT/US2020/044592 on Jul. 31, 2020, now abandoned.

(Continued)

(51) Int. Cl.

| | |
|---|---|
| ***A61B 34/20*** | (2016.01) |
| ***A61B 17/00*** | (2006.01) |
| ***A61M 25/09*** | (2006.01) |

(52) U.S. Cl.

CPC ........ *A61B 34/20* (2016.02); *A61B 17/00234* (2013.01); *A61M 25/09* (2013.01);

(Continued)

(58) Field of Classification Search

CPC .............. A61B 34/20; A61B 17/00234; A61B 2017/003; A61B 2034/2051; A61B 2034/2061; A61B 17/221; A61B 2017/22042; A61B 2034/2046; A61B 2034/2063; A61M 25/09;

(Continued)

(56) References Cited

U.S. PATENT DOCUMENTS

| | | | |
|---|---|---|---|
| 7,097,648 | B1 | 8/2006 | Globerman et al. |
| 9,968,761 | B2 | 5/2018 | Brecker |

(Continued)

FOREIGN PATENT DOCUMENTS

| | | | |
|---|---|---|---|
| CN | 102665541 | A | 9/2012 |

OTHER PUBLICATIONS

European Patent Office, Extended European Search Report dated Jun. 30, 2023 in European Patent Application No. 20847163.1, 10 pages.

(Continued)

*Primary Examiner* — Sanjay Cattungal

(74) *Attorney, Agent, or Firm* — Bookoff McAndrews, PLLC

(57) ABSTRACT

A guide wire that has an atraumatic and flexible loop that expands within a vessel, with indicators that indicate the degree of expansion. The indicators are used to determine the degree of expansion through the use of radio-opaque markers, hydraulic, and electrical signals. The guide wire enables safe passage into target vessels while providing user feedback on inadvertent passage into side branches and diseased segments.

21 Claims, 13 Drawing Sheets

Related U.S. Application Data

(60) Provisional application No. 62/881,252, filed on Jul. 31, 2019.

(52) U.S. Cl.
CPC . *A61B 2017/003* (2013.01); *A61B 2034/2051* (2016.02); *A61B 2034/2061* (2016.02); *A61M 2025/09183* (2013.01)

(58) Field of Classification Search
CPC .... A61M 2025/09183; A61M 25/0041; A61M 2025/09175
See application file for complete search history.

(56) References Cited

U.S. PATENT DOCUMENTS

| | | | | |
|---|---|---|---|---|
| 11,583,353 | B2 * | 2/2023 | Soper | G06T 3/14 |
| 2002/0062203 | A1 | 5/2002 | Gilboa | |
| 2003/0018251 | A1 * | 1/2003 | Solomon | G16H 50/30 600/427 |
| 2004/0152974 | A1 * | 8/2004 | Solomon | A61B 34/20 600/509 |
| 2007/0016068 | A1 | 1/2007 | Grunwald et al. | |
| 2008/0097476 | A1 | 4/2008 | Peh et al. | |
| 2009/0018566 | A1 | 1/2009 | Escudero et al. | |
| 2009/0326368 | A1 | 12/2009 | Zaslavsky et al. | |
| 2011/0015533 | A1 | 1/2011 | Cox et al. | |
| 2012/0271339 | A1 | 10/2012 | O'Beirne et al. | |
| 2014/0264081 | A1 * | 9/2014 | Walker | G01B 11/14 250/206.1 |
| 2015/0290432 | A1 | 10/2015 | Matthews et al. | |
| 2016/0346452 | A1 * | 12/2016 | Gilbert | A61M 1/369 |
| 2017/0348512 | A1 * | 12/2017 | Orr | A61M 25/0041 |
| 2018/0360533 | A1 * | 12/2018 | Olson | A61B 34/20 |
| 2018/0360534 | A1 * | 12/2018 | Teplitsky | A61B 5/02055 |
| 2019/0216447 | A1 * | 7/2019 | Bailey | A61M 25/00 |
| 2019/0365278 | A1 * | 12/2019 | Ludwin | A61B 5/062 |
| 2020/0078096 | A1 * | 3/2020 | Barbagli | A61B 34/20 |
| 2020/0129219 | A1 * | 4/2020 | Olson | A61F 7/00 |
| 2020/0197097 | A1 * | 6/2020 | Govari | A61B 5/6869 |
| 2020/0375617 | A1 * | 12/2020 | Govari | A61B 17/24 |
| 2022/0175269 | A1 * | 6/2022 | Lu | A61B 5/6851 |
| 2024/0033470 | A1 * | 2/2024 | Olson | A61M 25/0032 |

OTHER PUBLICATIONS

Chinese Patent Office, Office Action dated May 24, 2023 with English translation in Chinese Patent Application No. 202080064129. 2, 10 pages.
WIPO, U.S. International Search Authority, International Search Report and Written Opinion mailed Oct. 22, 2020 in International Patent Application No. PCT/US2020/044592, 9 pages.

* cited by examiner

FIG. 2A
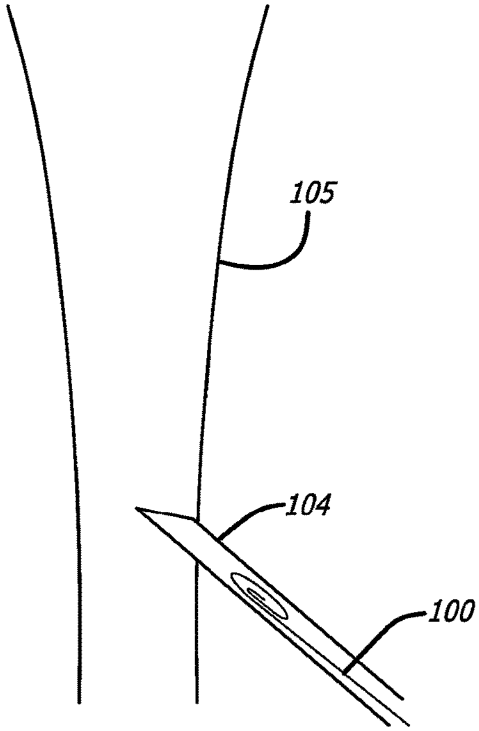
FIG. 2B
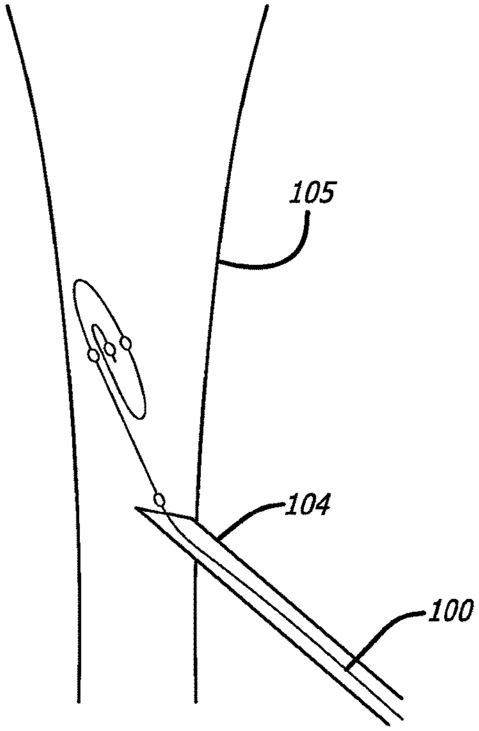
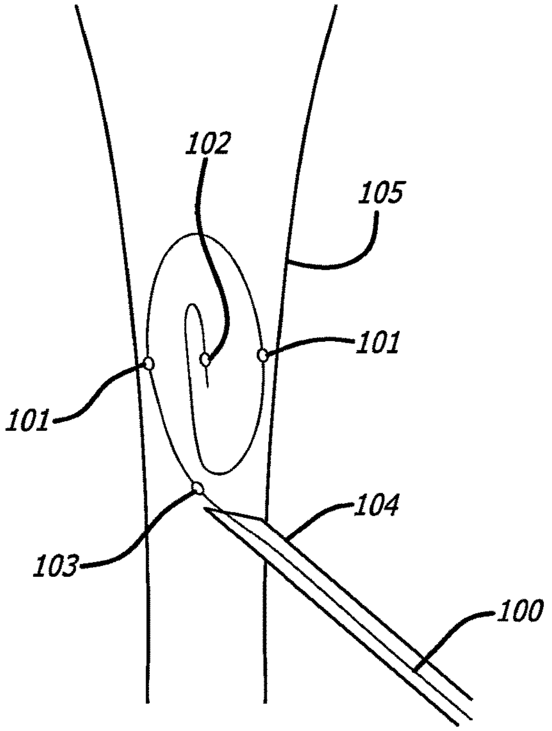
FIG. 2C
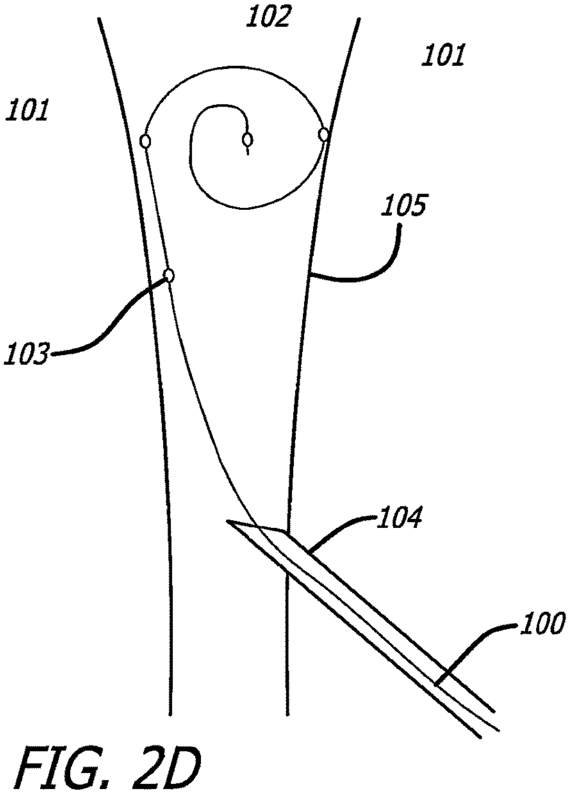
FIG. 2D

FIG. 3A
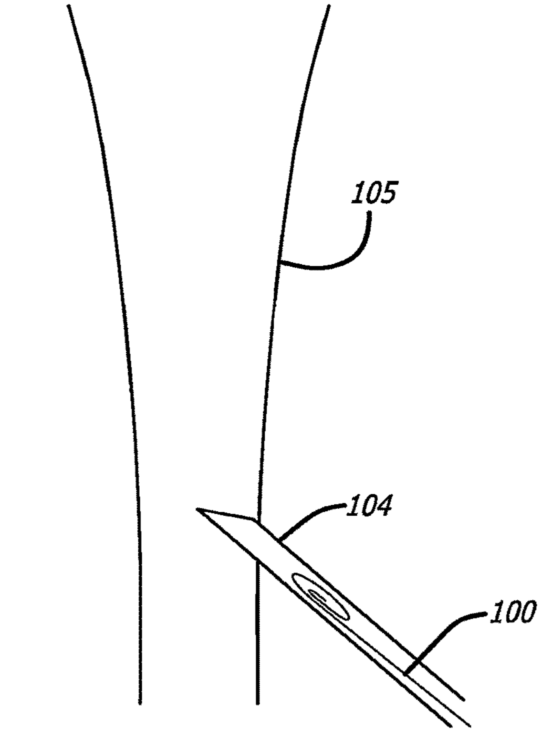
FIG. 3B
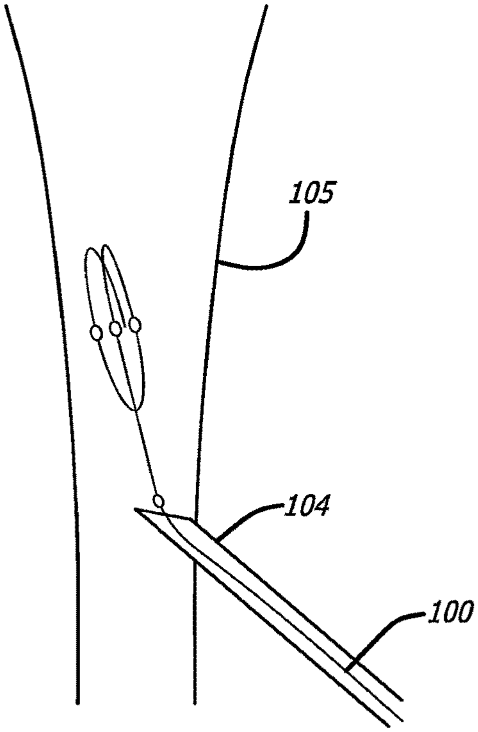
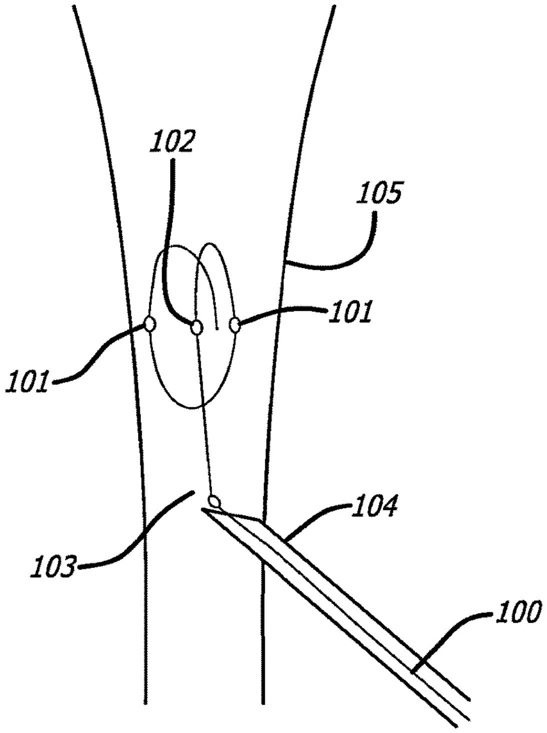
FIG. 3C
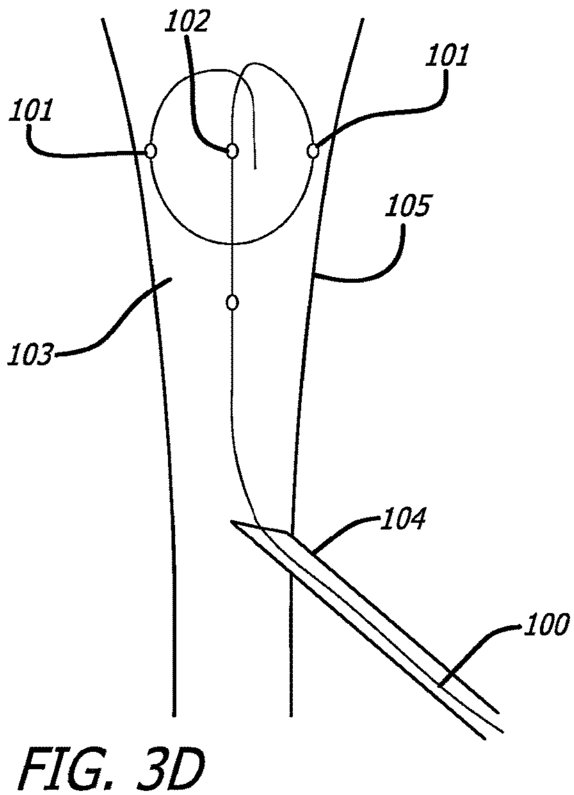
FIG. 3D

DEVICES AND METHODS FOR GUIDE WIRE PLACEMENT

RELATED APPLICATIONS

This application is a continuation of U.S. patent application Ser. No. 17/597,883, filed Jan. 27, 2022, entitled Devices And Methods For Guide Wire Placement, which is a National Stage Entry of PCT Application No. PCT/US2020/044592, filed Jul. 31, 2020, entitled Devices And Methods For Guide Wire Placement, which claims benefit of and priority to U.S. Provisional Application No. 62/881,252, filed Jul. 31, 2019, entitled Device For Safe Guide Wire Placement, all of which are hereby incorporated by reference.

FIELD OF THE INVENTION

The present invention relates to devices and methods to facilitate placement of a guide wire. More specifically, the invention relates to devices and methods to place a guide wire within a vascular structure with or without the use of adjunctive imaging methods such as fluoroscopy or similar equipment.

BACKGROUND OF THE INVENTION

For percutaneous medical procedures, there is a need to place devices, tools, or similar equipment into one or more blood vessels with the use of needles and wires. These techniques require direct insertion of the needle through the skin into the blood vessel, with or without imaging guidance (e.g. ultrasound, fluoroscopy, etc.), followed by passage of a guide wire into the lumen of the vessel.

The guide wire is then used to place additional equipment, such as vascular sheaths, catheters, or tools that can be used to treat a wide variety of conditions. Examples of such conditions include heart failure or shock, valvular heart disease, arrhythmias, congenital defects, peripheral vascular disease, stroke, aneurysmal defects, among others.

In traditional procedures, the guide wire is placed in the vessel and advanced, and its position may or may not be confirmed with imaging tools (e.g., fluoroscopy). During this advancement, inadvertent placement into locations besides the target vessel may occur. Such unintended locations include side branches or diseased segments (e.g. atheroma). When the guidewire is placed in such unintended areas, bodily injury may occur, either from the guidewire placement itself, or from subsequent placement of sheaths, devices, or tools that rely on directionality of the guide wire for accurate positioning.

In view of the foregoing, there is a need for methods and devices to place guide wires safely. This need includes safe placement from the point of initial entry into the body, during its advancement through the vasculature and to its final destination in the target vessel. This need also includes safe placement performed either with or without adjunctive imaging procedures and tools.

BRIEF SUMMARY OF THE INVENTION

The following is a summary of one or more embodiments of the present disclosure and provides a basic understanding of such embodiments. This summary is not an extensive overview of all contemplated embodiments and is intended to neither identify key or critical elements of all embodiments, nor delineate the scope of any or all embodiments.

The present invention relates to systems and methods for placing a guide wire in a blood vessel, which typically is an artery or vein. The present disclosure describes a device that improves the safety of the passage of a guide wire as it travels in vessels toward the heart. The safe passage of guide wires is desired to minimize the risk of harm as tools or devices (e.g., catheters, vascular sheaths) are introduced into blood vessels for treatment of a variety of cardiac, vascular, and neurologic diseases, among others. The present invention enables the safe passage of the guide wire by providing visible, tactile, and spatial feedback to the operator.

The present invention enables a person of skill and training less than that of a licensed medical doctor or practicing physician, e.g., a first responder, to safely pass a guidewire into a patient. The access could be through any vessel, including femoral access of either a femoral artery or femoral vein, or other peripheral vasculature. The invention minimizes the need for visualization systems such as X-ray Fluoroscopy and ultrasound. The invention reduces the time needed to place the guidewire and therefore reduces the time in which therapy can be performed on the patient. The invention enables better judgment on device position in the body with both internal and external location sensing.

In one embodiment, the guide wire may include a flexible loop that self-expands as it advanced into larger vessels, and contraction of the loop occurs when it is advanced into diseased segments or smaller vessels. As vessels typically become larger when traveling towards the heart, the loop expands as the guide wire has been advanced freely into the target vessel. If the guide wire is placed in a diseased segment(s) in the target vessel or inadvertently placed in small branches, contraction of the loop occurs and is visible on fluoroscopy. In some embodiments, the loop may be singular or multiple or pigtail, and uni-directional or multi-directional. In one embodiment, the loop contains radio-opaque markers that demonstrate expansion or contraction of the loop.

In one embodiment, electronic generators and sensors may be located in the loop that create currents for resistance or impedance measurement. These electrical signals are carried by the guidewire to an external machine or computer that processes them and then determines distances between the generators and sensors. These distances vary with expansion and contraction of the loop. The external machine or computer therefore enables the operator to know if the guide wire is being passed safely and freely into large vessels, or the guide wire has inadvertently entered diseased segments of small vessels. Thus, in one embodiment, the guide wire can be passed safely without the use of adjunctive imaging tools (e.g. fluoroscopy), which may either not be available or not desired.

In another embodiment, radiofrequency identification tags may be used to externally determine the location of the wire in the body.

In yet another embodiment, external magnets may be used to move the wire within the body.

One example of a use of an embodiment is the placement of balloon-flotation catheters for measurement of intra-cardiac pressures often needed for emergency life-saving hemodynamic support therapy (e.g. extracorporeal membrane oxygen support or ECMO). Another example of a use is in situations outside of an imaging suite or outside of a hospital. Another example of use is in connection with large bore vascular access for fluid administration, among others.

In another embodiment, the wire may contain durometers or similar pressure indicators. The pressure signals are transmitted to an external device or computer and interpreted to indicate whether or not the guide wire is within the target vessel.

In another embodiment, a reusable piece of equipment is used to take measurements used as feedback by a medical provider for diagnosis and treatment of a patient. This equipment is capable of measuring, recording, and transmitting patient data to medical professionals and can include, but is not limited to, heart rate, blood pressure, blood flow, oxygen saturation, respiration rate, and others. In one embodiment, this data is sent over wireless communication to a medical professional in a remote location.

In another embodiment, a reusable piece of equipment is used by a medical provider to deliver therapy to a patient. In one embodiment, this equipment controls and administers therapy, such as, but not limited to, heart rate or rhythm control, drug delivery and others.

In another embodiment an external sensing pad or pads may be attached or positioned on the torso of the patient to facilitate collection of patient data, administering therapy to the patient, and providing location and positioning information of the internal apparatus. These external pads could be made to a single unitary member or have many (e.g. 50 or more)\individual locations upon the body. In one embodiment, the pad or pads includes, but are not limited to, sensors for position identification, resistance measurement, magnetic detection, radiofrequency detection, grounding of circuits, temperature, presence of energy fields, transmission of energy, etc.

In another embodiment, a tapered coil having an inductance change as an indicator of diameter change may be used. The inductance of a coil is dependent on its geometry. As a tapered coil is passed through different vessel sizes the shape of the coil changes (e.g., it compresses or lengthens) and thereby changes its inductance. Where inductance is measured, it can be used to indicate a position of the coil in a vessel.

In another embodiment, strain gauges are used to detect a change in vessel diameter. In one embodiment, a coil element serves as the guidewire and the coil itself could be a strain gauge or the construction of the coil member would incorporate a strain gauge. Strain gauges change their resistance as force is applied to them. As the coil is moved through different size vessels its coil shape changes, thereby exerting different levels of strain on the sensors. In one embodiment, the strain gauge sensor is accessed from outside the body through the use of trifilar wires that are incorporated into the guide wire.

In another embodiment, sonar and or laser is used to measure the diameter of the vessel. A sonar or laser sensor as known in the art is positioned at the tip area of the guidewire and is powered by trifilar wire.

In another embodiment, force to expand or compress an expanding member of the guidewire at the tip of the device could be measured. This force could also be measured at the proximal end of the device.

In another embodiment, the invention comprises a multiple component system that may include a set of nested members, an inner guidewire, an expanding element, and an outer guide catheter or sheath. The assembly could have from 1 to 100 different components. In one embodiment, the expanding member changes in length during expansion and collapse. In one embodiment, the changes in length are correlated to a known diameter of the expanding member. As a result, measuring the change in length correlates to a known change in diameter.

In another embodiment, the device incorporates a steerable element at the tips for navigation controlled from the back end of the wire or apparatus. The element could be a pull wire mechanism.

In another embodiment, the device includes a wire inside a catheter which holds the sensors together and then is unsheathed from the wire in order to "determine" the location of the wire as it is advanced. The catheter can be advanced and retracted over the wire to repeatedly test the location of the device.

In another embodiment, a tip of the wire senses contact with a wall or vessel plaque, and stiffness in the body of the wire then becomes soft. This change in stiffness can help avoid or minimize injury from the device. In one embodiment the wire is very soft and placed inside delivery catheter. The tip is retractable when contact with wall occurs. The soft wire could be gently advanced or repositioned.

The shape of the expanding member could be any expanding shape including, but not limited to, helical coil, coil, loop, multiple loop, closed end coil, open ended coils, spiral, multiple spirals and the like. The expandable member(s) could be positioned on the guidewire or on the sheath member.

Further alternative shapes of the expandable members could be any expanding shape including, but not limited to; one deflecting member captured on one end, two or more deflecting members captured on one end, one deflecting member captured on two ends, two or more deflecting members captured on two ends, spiral deflecting members, helical deflecting members, cage-like deflecting members, or combinations thereof.

The expanding members can be made from braided material, extruded material, laser cut material, metal, plastic, or other. The construction could be a unitary member or an assembly of different members.

In another embodiment the apparatus has multiple stiffness characteristics throughout its length. In one embodiment, variations in stiffness are adjustable by the user. In one embodiment, the length of the different stiffness regions is also adjustable. In one embodiment, the diameter of the apparatus is variable along its length. In one embodiment, the diameter is expandable throughout its length. In one embodiment, these features are optimized to facilitate tactile feedback to the user so as to enhance the user's ability to advance the wire without prolapse, ensuring the intended trajectory is achieved, and provide external indication of the status or position of the apparatus.

In another embodiment, resistance of an applied current between two or more locations on the device is used to measure the diameter of the vessel. In one embodiment, measurements occur at various locations of the apparatus. As the distance of the two locations changes a change in resistance is correlated thereto thus allowing the determination of vessel diameter or device position by the user.

In another embodiment ultrasound is incorporated into the system. The apparatus incorporates passive and or active features which allow the detection of an advancing member from an ultrasound device applied externally to the patient. Such features known in the art include surface coatings, active vibration, balloons, etc. such features allow a user to observe a guidewire position and/or to better observe blood vessels ahead of the guidewire's direction.

In another embodiment magnets are incorporated into the apparatus and on an external detecting device located on the patient. In one embodiment, magnets are disposed on the guidewire and external magnet sensors (such as pads) are placed along the path to the heart. When the magnet on the device passes under the sensor, it indicates to the user its location. Such indication could be turning on an LED or sending data to another piece of equipment.

In another embodiment, the sensors are built into the patient's bed, cart, transport vehicle, or other material holding or carrying the patient, either in the ambulance or the hospital. The guiding/alert system is integrated into the holding material such that no other system is needed to provide access and guidewire direction into the patient.

In an alternative embodiment, a magnet sensor (e.g., a hall sensor) is disposed on a guide wire and the clinician places external magnet patches on the patient along the route to be expected for the guide wire. The external equipment outside the patient reads the magnetic field and when the field strength is increased so as to indicate the location of the device. In another embodiment, a strong external magnet guides the wire up the vasculature. In one embodiment, the user traces the external magnet from the leg up towards the heart to move the wire. The system indicates if the magnetic force on the wire has changed or been lost and thereby indicates whether the wire has encountered an obstacle or is not moving/tracking properly.

In another embodiment radio frequency (RF) detection is used to determine position. In one embodiment, surface patches with RF homing beacons are placed on the patient and used to detect signal strength. In one embodiment, the principle of triangulation used with cell phones and Wi-Fi devices (but on a much smaller scale) to determine position, is used. In one embodiment, at least 3 sensors are placed outside the body which then translate the information into a visual of the location of the guidewire in the body. The detection method could go either way wire-to-patch, patch-to-wire.

In another embodiment the apparatus includes a balloon having integrated electrical sensors. In one embodiment, fluid used to fill the balloon is conductive and the amount of fluid in the balloon yields a specific electric field which is measured and correlated to a size of the balloon. In one embodiment, the balloon is shaped to allow for passage of blood flow and not restrict the flow. The electrodes or sensors could be mounted on a flotation balloon that is designed to travel with the blood flow.

In one embodiment, the guide wire includes components that allow gathering of patient information useful for diagnosing and treating the patient. Such components, as known in the art, could measure data such as heart rate, blood pressure, blood flow, oxygen saturation, respiration rate, and others. n one embodiment, the guide wire includes components that allow delivery of therapy to a patient including, but not limited to, heart rate management, blood pressure management, blood flow, oxygen saturation, respiration rate, drug delivery and others. In one embodiment the apparatus is used to pace the patient's heart.

In one embodiment there is a device for interventional vascular procedures that includes: a guide wire having a distal region and a proximal region; a flexible mechanism disposed along said distal region of said guide wire; a plurality of sensors disposed along said distal region of said guide wire and associated with said flexible mechanism; said plurality of sensors configured to generate signals correlating to spatial positional changes of each of said plurality of sensors when said distal region is present in a vessel.

In one embodiment of the invention there is a system for an interventional vascular procedure that includes an access sheath; a guide wire configured for use with said access sheath; said guide wire having a distal region and a proximal region; a flexible mechanism disposed along said distal region of said guide wire; a plurality of sensors disposed along said distal region of said guide wire and associated with said flexible mechanism; said plurality of sensors configured to generate signals correlating to spatial positional changes of each of said plurality of sensors when said distal region is present in a vessel; and an external equipment for receiving and processing signals of said plurality of sensors.

In one embodiment of the invention, there is a method of intervening in the vasculature of a patient comprising cannulating said patient; introducing a guide wire into said vasculature of said patient; moving said guide wire toward a heart region of said patient; measuring a dimension of said vasculature with said guide wire during said movement of said guide wire; determining changes in said dimension of said vasculature; and, adjusting movement of said guide wire based on changes in said dimension of said vasculature.

While multiple embodiments are disclosed, still other embodiments of the present invention will become apparent to those skilled in the art from the following detailed description, which shows and describes illustrative embodiments of the invention. As will be realized, the various embodiments of the present invention are capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as invention, it is believed that the invention will be better understood from the following description taken in conjunction with the accompanying Figures, in which:

FIGS. 2A, 2B, 2C, and 2D show passage of a guide wire embodiment and its expansion as it moves into large vessels in accordance with the present invention.

FIGS. 3A, 3B, 3C, and 3D, show passage of a guide wire embodiment and its expansion as it moves into large vessels in accordance with the present invention.

DETAILED DESCRIPTION

The present invention relates to systems and methods for enabling safe passage of guide wires to facilitate vascular access. The embodiments are applicable to any vascular access, whether percutaneous, surgical cut-down, or similar means, in which passage of equipment into cardiovascular structures is desired.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Figure 1A:
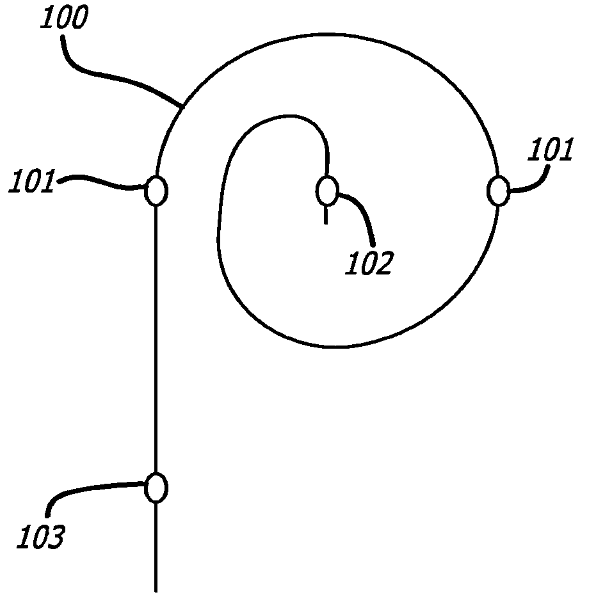
FIGS. 1A, 1B, 1C, and 1D show embodiments of a guide wire with alternate configurations in accordance with the present invention.

FIG. 1A shows a guide wire 100 with distance sensors 101, 102, and 103. The guide wire loop is self-expanding and becomes larger if not constrained by the vessel wall. The looped tip is soft and atraumatic. The distance sensors 101 indicate the width of the guide wire loop and thus indicates the width of the vascular structure where the loop is located at a given time as discussed in more detail below.

Figure 1B:
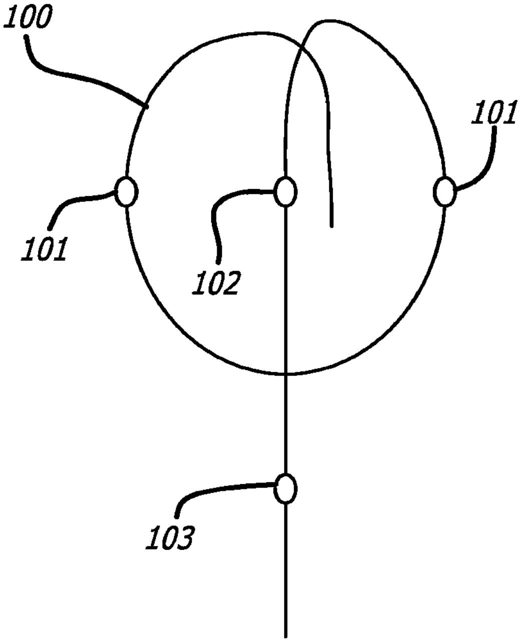
Figure 1C:
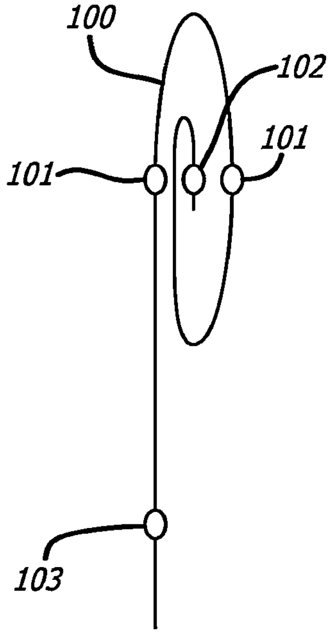
Figure 1D:
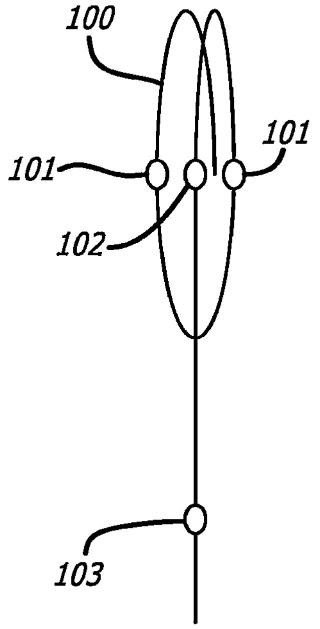

The central sensor 102 is an additional indicator whose distance to sensors 101 can be measured. In this embodiment, the distance from sensors 101 to 103 is used to indicate bending of the wire, which may occur if the wire is not freely moving into the vessel. FIG. 1B shows a different embodiment of the loop structure. In this embodiment, the distance from sensors 102 to 103 is used to indicate bending of the wire. FIGS. 1C and 1D show compression of these embodiments as they are passed through an access needle into the blood vessel. FIGS. 1C and 1D also show compression of these embodiments that would occur if they are advanced into diseased segments of a vessel or simply into smaller vessels (e.g. side branches).

FIG. 2A show an access needle 104, a vessel 105, and the guide wire 100 being placed. FIG. 2B shows compression of the guide wire 100 while it is in the small width of the access vessel. FIG. 2C shows expansion of the guide wire 100 as it is advanced into vessel 105. As the guide wire 100 self-expands the indicators 101 become further apart. The distance between sensors 101 and 103 is maintained due to the unconstrained nature of the guidewire, i.e., when there is no kinking or significant bending of the wire. FIG. 2D shows the guide wire 100 fully expanded with maximal width indicated by sensors 101 and lack of kinking or significant bending by the distance between sensors 101 and 103. The guide wire 100 can then be used to safely place additional equipment such as vascular sheaths or catheters.

FIGS. 3A, 3B, 3C, and 3D show another embodiment. As in FIG. 2, there is an access needle 104, a vessel 105, and the guide wire 100 being placed. FIG. 3B shows compression of the guide wire 100 while it is in the small width of the access vessel. FIG. 3C shows expansion of the guide wire 100 as it is advanced into vessel 105. As the guide wire 100 self-expands the indicators 101 become further apart. The distance between sensors 102 and 103 is maintained when the guide wire is unconstrained, i.e., when there is no kinking or significant bending of the wire. FIG. 3D shows the guide wire 100 fully expanded with maximal width indicated by sensors 101 and lack of kinking or significant bending by the distance between sensors 102 and 103. The guide wire 100 can then be used to safely place additional equipment such as vascular sheaths or catheters.

FIG. 4 shows how the embodiments indicate passage into areas besides the target vessel 105. In FIG. 4A, one embodiment of the guide wire 100 is introduced and begins to expand in the vessel 105. With further passage, the guide wire 100 inadvertently enters side branch 106. In FIG. 4B, as the guide wire 100 is passed further, contraction of the loop occurs and the sensor indicators become closer in distance, thereby indicating to the operator that the vessel size is becoming smaller and inadvertent passage has occurred. The guide wire 100 can then be retracted and repositioned into target vessel 105. In FIG. 4C, a diseased segment 107 is present. The guide wire 100 interacts with this diseased segment 107 during passage. In FIG. 4D, with additional passage of guide wire 100, bending of the wire 100 occurs, and this bend is indicated by loss of distance between sensors 102 and 103. The guide wire 100 can then be retracted and repositioned in target vessel 105.

It is important to note that the sensors disclosed throughout this specification can be of multiple types, including but not limited to, electrical, magnetic, RF, strain gauge, hydraulic, and capable of conducting impulses, all as known to those of skill in the art. These sensors provide detection of wire positioning, twisting or bending, contraction, expansion, or excessive force during advancement.

In a preferred embodiment the sensors referred to herein are sensors used to measure resistance of applied current. More specifically, resistance measured between two or more sensors is used to measure or calculate the diameter of the vessel as is more fully disclosed below. Sensors for measuring resistance would, in one embodiment, be electrodes that are installed at various locations on a guide wire 100 as also more fully described below. The resistance of a circuit formed by two or more electrodes in a blood field is dependent upon the distance between the electrodes. The change in either current or voltage is measured and changes in the values are then calibrated to distance-change in the electrodes. This is similar to catheters that are used to ablate the heart where the electrode contact is determined by measuring the impedance of the system. This measurement is dependent on the tissue contact and electrode spacing and is then compared to the known value of the impedance in a blood field without tissue contact. The principle here is to keep the blood field a constant and vary the distance of electrode and determine the difference from known positions, starting positions, final positions, or change. Exemplary systems and the principles on which they are based and which are usable in connection with the present invention are found in, for example, U.S. Pat. Nos. 6,569,160; 9,149,225 and U.S. Publication Nos. 20140142398; 20110082383, and "Novel Method for Electrode-Tissue Contact Measurement With Multi-Electrode Catheters" R. van Es et al. Europace (2018) 20, 149-156, the entire contents of each being incorporated herein by reference.

As the distance of between sensors is changed there is a change also in resistance. This change in resistance is correlated to vessel diameter or device position feedback which is observed by the user.

The electrodes may be individually wired or coupled in sequence to achieve the desired output. External surface patches as also described below are also usable to detect the current changes due to changing resistance.

In another embodiment ultrasound is incorporated into the system. The apparatus incorporates passive and or active features that allow the advancing member to be detected from an ultrasound device applied externally to the patient. The features known in the art such as surface coatings, active vibration, balloons 2300 and the like could be implemented. These features would allow for the clinician to see where the guidewire is and better direct it or to see the blood vessels ahead of the guidewire to ensure going in the correct direction.

In another embodiment magnets are used in the apparatus and on an external surface device. Powerful magnets are applied on the guidewire at the identified sensor locations or at external magnet sensor pads as described below placed along the path to the heart. When the device location is passed under the sensor it indicates to the user its location, by, for example, turning on an LED or sending the data to another piece of equipment to notify of a position.

The inverse could be done as well where the magnet sensor (hall sensor) is attached to the guide wire and the clinician puts magnet surface patches (as described below) along the route. The external equipment outside the patient would read out the magnetic field and detect the field strength and indicate location of the device.

In another embodiment, radio frequency (RF) detection is used to determine position. Surface patches (as described below) with RF homing beacons are used to detect signal strength. The principle of triangulation that is used with cell phones and Wi-Fi devices, but on a much smaller scale, can be used. At least 3 sensors are placed outside the body, then the outside equipment processes the information into a visual image the device is located in the body. The detection method could go either wire-to-patch, patch-to-wire.

Figure 5:
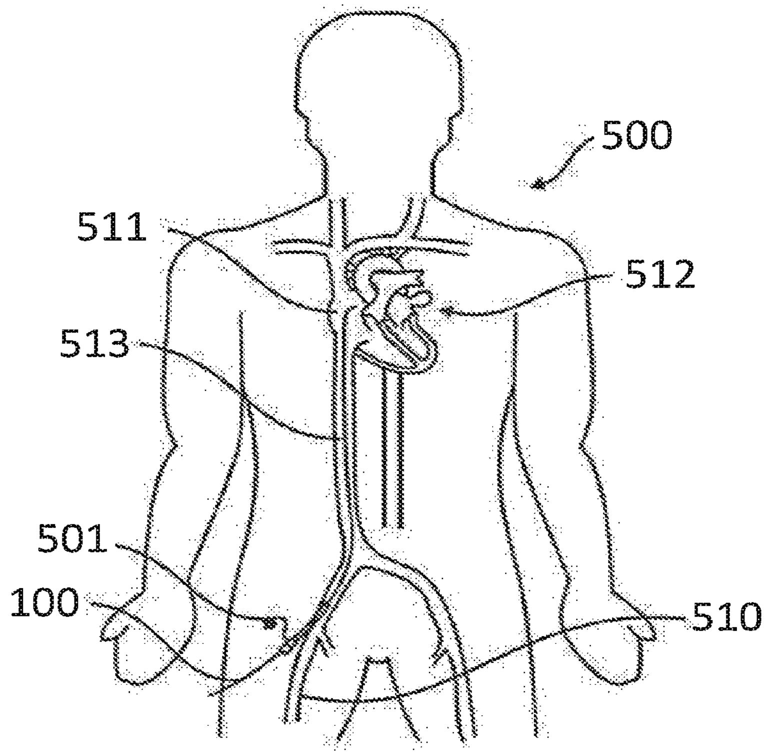
FIG. 5 is a rendering of a human patient with an embodiment of the present invention located in the venous vasculature.

With reference to FIG. 5, in one embodiment, the guide wire 100 is placed in the venous vasculature 510 and 513 of the patient 500. The guide wire 100 is placed into the right atrium 511 through the IVC 513 and femoral vein 510. It is introduced into the femoral vein 510 through an access cannula 501.

Figure 6:
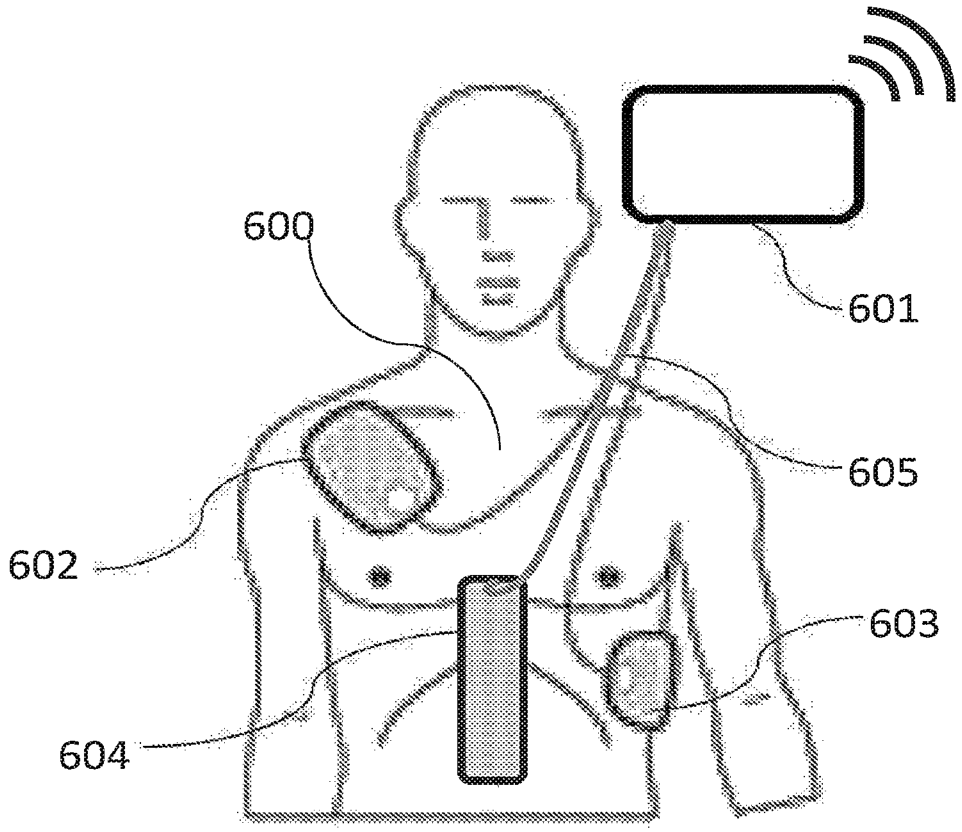
FIG. 6 is a rendering of a human patient with an embodiment of the present invention placed on an external aspect of the torso of a patient as well as external equipment representation in accordance with the present invention.

With reference to FIG. 6, external surface pads 602, 603 and 604 are placed on a human patient 500 on the external surface of the patient's torso 600 and are used to obtain signals from the sensors on the guidewire. An external equipment controller or monitor 601 is connected to the surface pads with cables or wires 605 to facilitate communication. The system, however, could be wireless and the patches could transmit the data to the external equipment 601 wirelessly.

In one embodiment, the external equipment 601 is used to take measurements from the sensors on the guidewire 100 and convert the measurements into feedback that a medical provider can use to diagnosis and treat a patient. Multiple modes of sensing are contemplated by the present invention as discussed through the specification.

The external equipment 601 is capable of receiving, processing, measuring, recording etc. data from said patient and said sensors and to transmit information to medical professionals for diagnosis and therapy needs. Such data can relate to heart rate, blood pressure, blood flow, oxygen saturation, respiration rate, and other parameters. This data may also be sent over wireless communication to a medical professional at a remote location.

In another embodiment, the external equipment 601 is used by a medical provider to deliver and control therapy to a patient. Such therapy could include heart rate monitoring or control, drug delivery and other therapies.

In another embodiment, the external surface pads 602, 603, 604 are attached or positioned on the torso of the patient to facilitate collection of patient data from sensors on the guide wire 100. These external pads 602, 603, 604 could be made into a single unitary member or replaced with many, e.g. 50, pads placed individual locations upon the body.

The external surface pads 602, 603, 604 contain a device or devices to measure aspects generated by the sensors on guide wire 100. Such measuring can include, position identification, resistance measurement, magnetic detection, RF detection, grounding of circuits, temperature, presence of energy fields, as well as others not specifically enumerated here but otherwise known in the art.

In one embodiment, the guide wire consists of features that would allow it gather information about the patient that a medical professional could use to diagnose and treat the patient such as but not limited to; heart rate, blood pressure, blood flow, oxygen saturation, respiration rate, and others.

In one embodiment, the guide wire includes features that would allow it to deliver therapy to patient such that a medical professional could treat the patient such as but not limited to; heart rate, blood pressure, blood flow, oxygen saturation, respiration rate, drug delivery and others. In one example, the apparatus could be used to temporarily pace the patient's heart.

Figure 7:
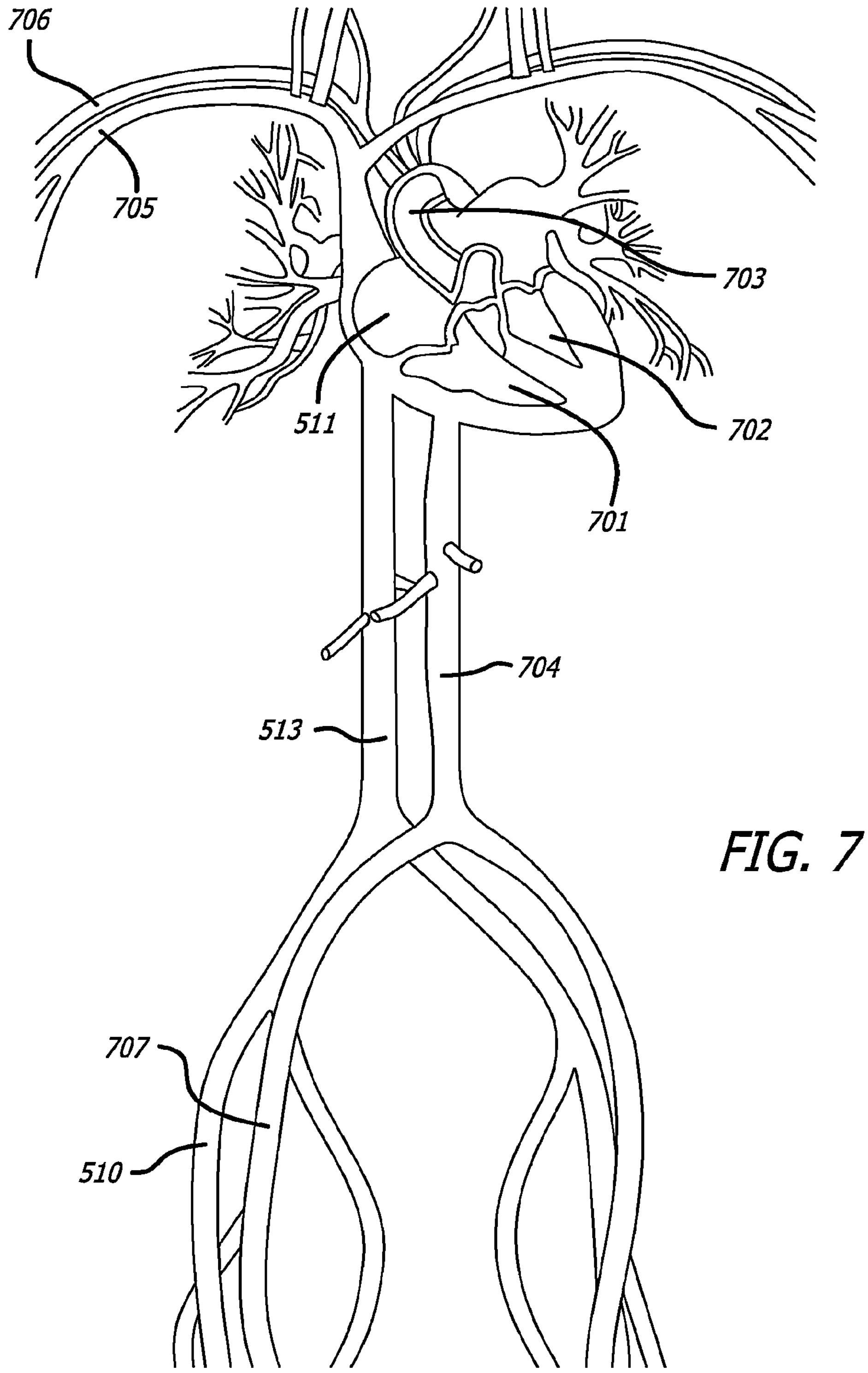
FIG. 7 is a rendering of a human vasculature in which an embodiment of the present invention is used.

Referring to FIG. 7, the guide wire 100 can be used in multiple lumens of the human vasculature, including, the inferior vena cava (IVC) 513, the abdominal aorta 704, the common iliac artery 707, the femoral vein 510, the right atrium 511, the right ventricle 701, the left ventricle 702, the aorta 703, the subclavian artery 706, and the subclavian vein 705.

Figure 8:
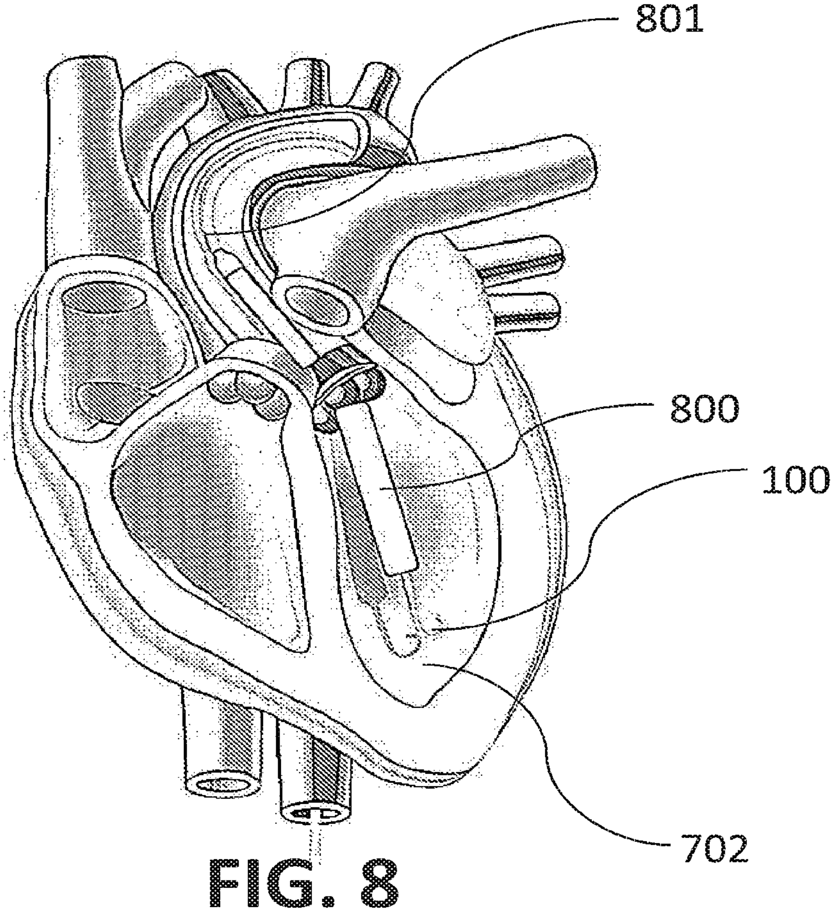
FIG. 8 is a rendering of a human heart in which an embodiment of the present invention is used.
Figure 9:
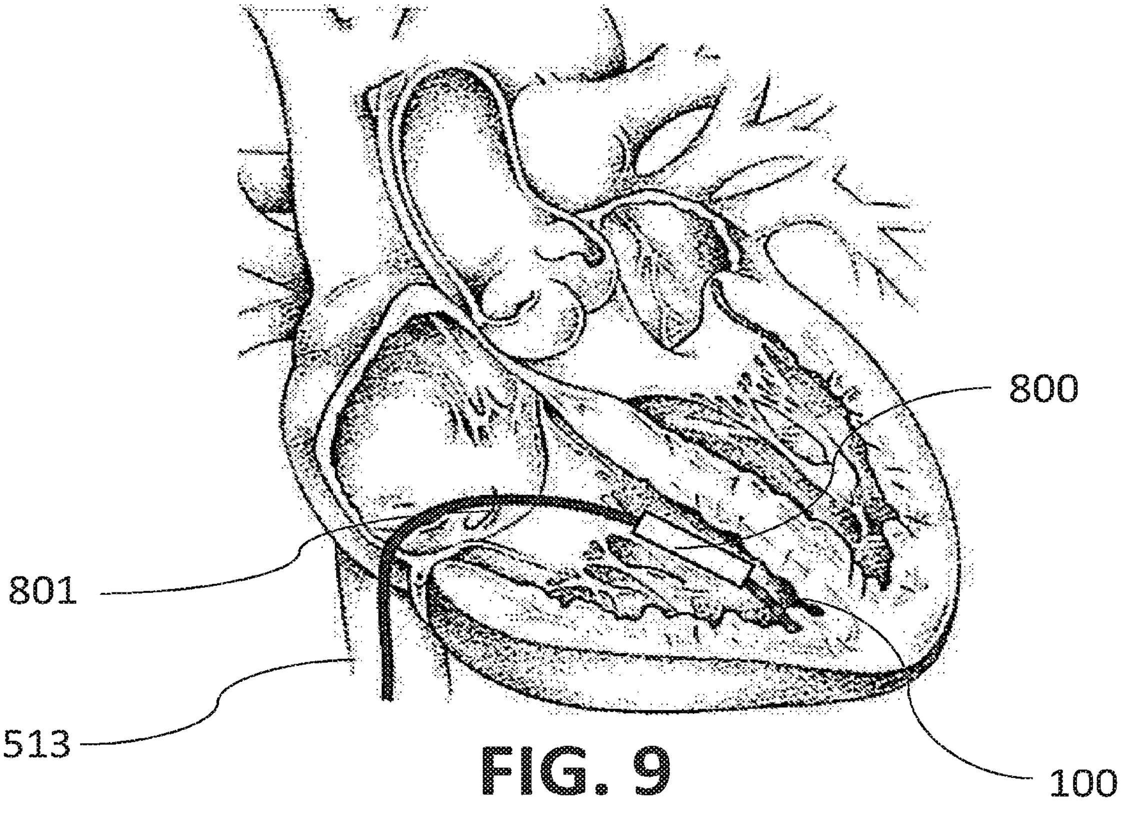
FIG. 9 is a rendering of a human heart in which an embodiment of the present invention is used.

Referring to FIGS. 8 and 9, a guide wire or guide catheter apparatus 801 is tracked into the heart with expandable member 800 near the distal tip. As will be appreciated by one of skill in the art, item nos. 801 and 800 are schematic views and are representations of multiple embodiments of the present invention as disclosed and discussed herein, including those of FIGS. 1-23.

In one embodiment, the tip of the guide wire 100 and expandable member 800 are placed into the left ventricle 702 while the body of the apparatus 801 remains in the aorta. In this position the device may be used for direct therapy to the cardiac tissues such as drug delivery and or electrical stimulation. FIG. 9 shows device 100 in the right ventricle through the IVC 513.

Figure 10:
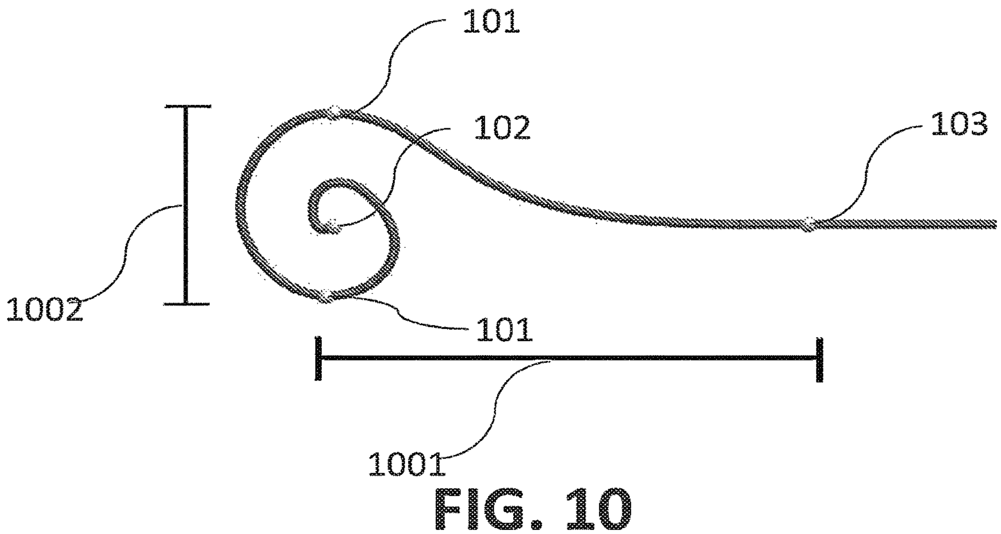
FIG. 10 is a side view of one embodiment in accordance with the present invention.

Referring to FIG. 10, an embodiment of guide wire 100 is shown in its resting, unconstrained state. In such a state, there is a known dimension 1001 between sensors 102 and 103 and a known dimension 1002 between sensors 101. During use, movement of the sensors 101, 102 and 103 will occur according to the nature of the vasculature in which the guide wire 100 is present. This movement of the sensors will generate sensor signals that are processed by the external equipment 601 to determine the change in dimensions 1001 and 1002 compared to the known dimensions. In a manner know to those of skill in the art, this change in dimensions 1001 and 1002 is used to calculate a diameter of the vessel in which the guide wire 101 is located at that time.

Figure 11:
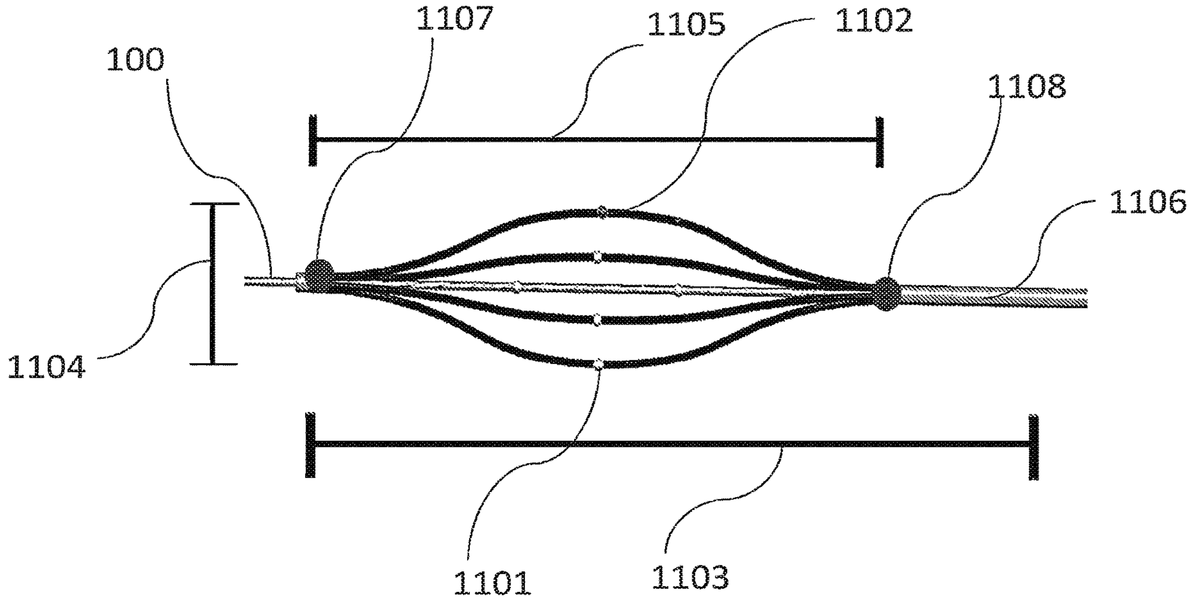
FIG. 11 is a side view of one embodiment in accordance with the present invention.

Referring to FIG. 11, an alternative embodiment of the guide wire 100 is shown in its resting and unconstrained state in which multiple struts are mounted on the tip of the guide wire 100 which form an expandable member 1102 on the tip of the guide wire 100. The guide wire includes sensors 1101, 1107 and 1108. Furthermore, there is a known dimension 1104 between sensors 1101, a known dimension 1105 between sensors 1107 and 1108 when the member 1102 is in an uncompressed state and a known dimension 1103 between sensors 1107 and 1108 when the member 1102 is in a compressed state.

Dimension 1103 is the distance between sensors 1107 and 1108 when the expandable member 1102 is compressed. As the member 1102 expands the distance between the sensors 1107 and 1108 is reduced to a distance 1105. This distance change correlates with a known diameter increase 1104, both which can be measured, and or calculated by the data collected from sensors 1107 and 1108 at their positions at any given time and/or the sensors 1101 on expandable member 1102 as is known to those of skill in the art.

In a manner similarly described with respect to FIG. 10, during use, movement of the sensors 1101, 1107 and 1108 will occur according to the nature of the vasculature in which the guide wire 100 is present. This movement of the sensors will generate sensor signals that are processed by the external equipment 601 to determine the change in dimensions 1104, 1105 and 1103 compared to the known dimensions. This change in dimensions 1104, 1105 and 1103 is used to calculate a diameter of the vessel in which the guide wire 101 is located at that time.

Figure 4A:
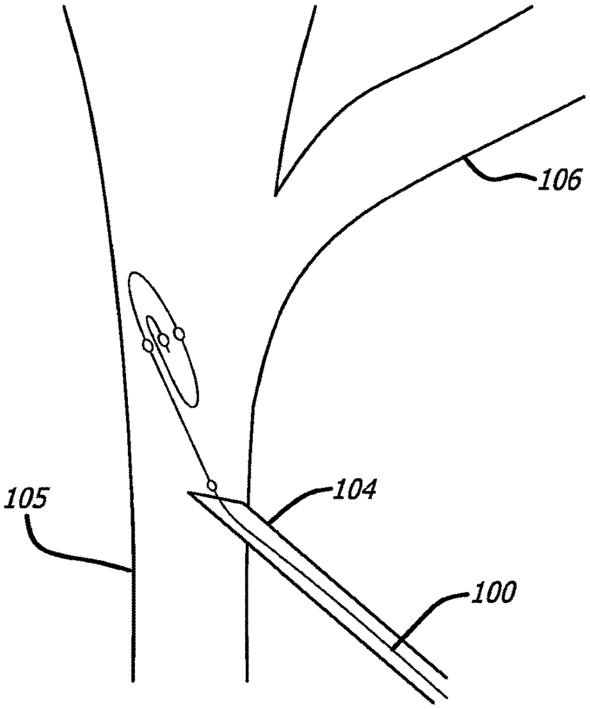
FIGS. 4A and 4B show contraction of a guide wire embodiment as it moves into smaller vessels in accordance with the present invention.
Figure 4B:
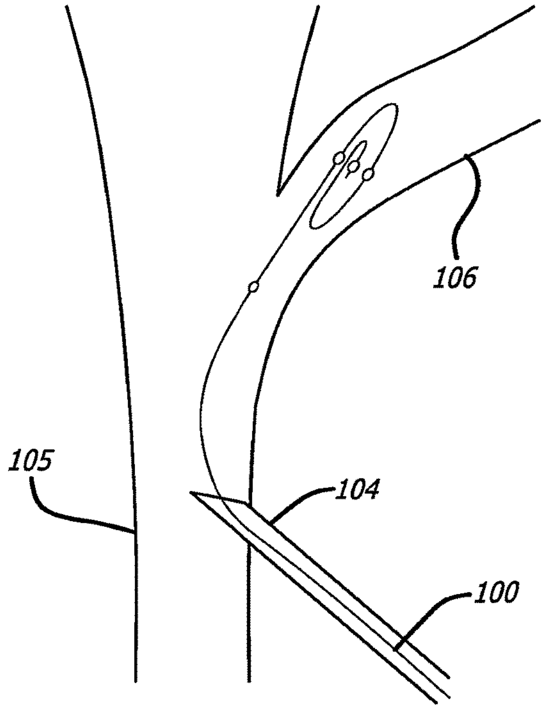
Figure 4C:
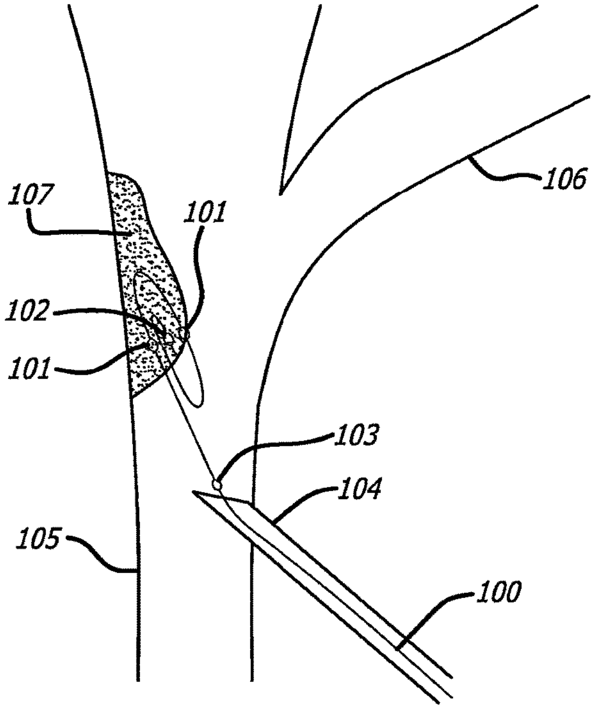
FIGS. 4C and 4D show bending of a guide wire embodiment due to interference of its free passage in a vessel, and how this lack of free passable is indicated by indicators that are either visible and/or provide electrical signaling that relay distances between them in accordance with the present invention.
Figure 4D:
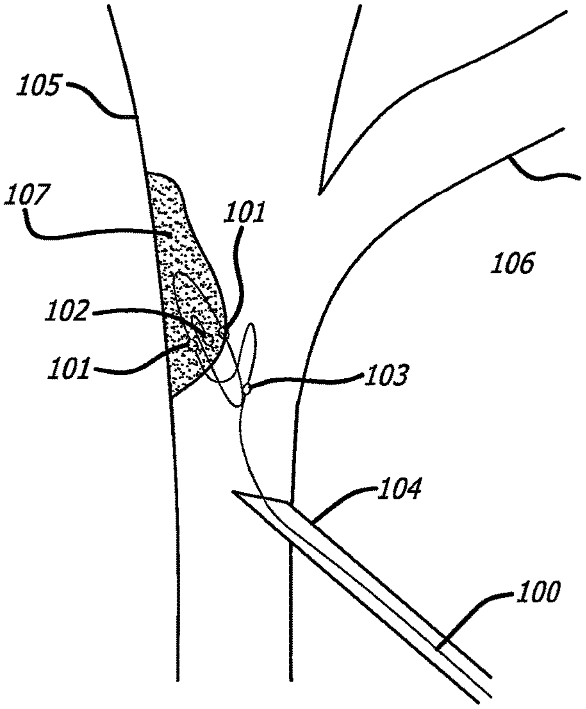

Also, the expanded configuration could inhibit the advancement of the apparatus into a vessel of smaller diameter in. For example, a guidewire could pass into a vessel smaller than the intended path as shown in FIG. 4B. An expanded member such as shown in FIGS. 10-23 might be of a larger diameter than that of the smaller vessel 106. The feedback to the user could be that of tactile resistance, electrical indication of a change in diameter or position and thus indicate to the user that the guidewire is directed in an undesired path.

Figure 12:
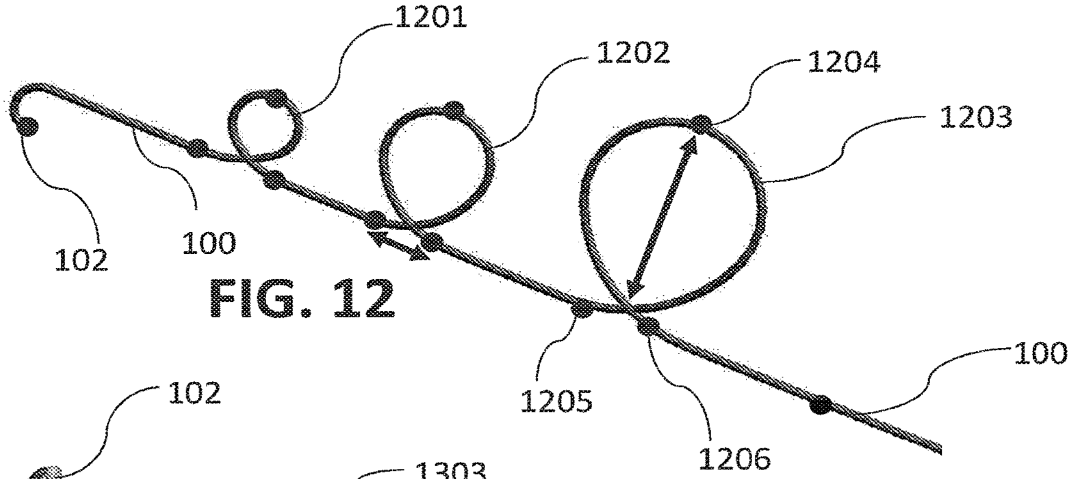
FIG. 12 is a side view of one embodiment in accordance with the present invention.

Referring to FIG. 12, an alternative embodiment of a guide wire 100 includes three loop members 1201, 1202, and 1203. In this embodiment the loops 1201, 1202 and 1203 increase in diameter along the length of the guide wire. However, the loop members could decrease in diameter along the length of the guide wire 100 tip, could be more or less in number and could be each of the same size as will be appreciated by one of skill in the art.

Each loop member includes sensors 1204, 1205 and 1206. In a manner that will be appreciated based on the discussion above with respect to FIGS. 10 and 11, the known dimensions between sensors (see arrows) will change, during use, depending on the configuration of the vessel in which the guide wire 100 is located at that time. The signals generated by the sensors 1204, 1205 and 1206 are processed by the external equipment 601 to determine the change in dimension compared to the known dimension. This change in dimension is used to calculate a diameter of the vessel in which the guide wire 101 is located at that time.

The presence of multiple loops 1201, 1202, 1204 may also be used to formulate a profile of the vessel along the length of the guide wire 100.

Also, the expanded configuration could inhibit the advancement of the apparatus into a vessel of smaller diameter or vessel with a diameter that has been comprised by disease such as atherosclerotic plaque as discussed above.

Figure 13:
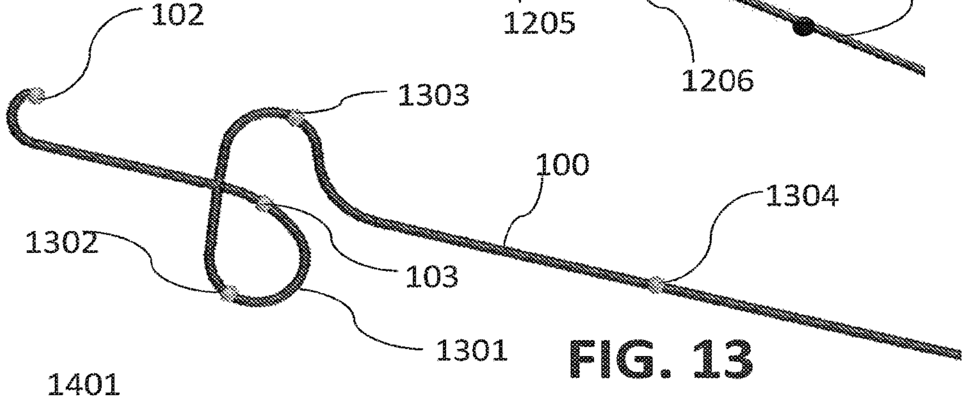
FIG. 13 is a side view of one embodiment in accordance with the present invention.

Referring to FIG. 13, an embodiment of guide wire 100 includes a non-linear path 1301 on which sensors 1302, 103 and 1303 are disposed. The guide wire 100 also includes sensors 1304, and 102 along the guide wire 100 length.

As with previous embodiments, there are known dimensions between sensors as described above. These dimensions will change, during use, depending on the configuration of the vessel in which the guide wire 100 is located at that time. The signals generated by the sensors 1302, 103, 1303, 102, 1304 are processed by the external equipment 601 to determine the change in dimension compared to the known dimension. This change in dimension is used to calculate, for example, a diameter of the vessel in which the guide wire 101 is located at that time.

For example, the signals associated with the dimension between sensors 102 and 1304 along with the signals associated with the dimensions between sensors 1302, 1303, and 103 in the non-linear section 1301 could yield an approximation of the vessel size and location while also yielding a shape that would not advance into a smaller vessel in which it was expanded, because the cross sectional dimension of the expanded configuration would be larger than that of the smaller vessel or vessel with a diameter that has been comprised by disease such as atherosclerotic plaque.

Figure 14:
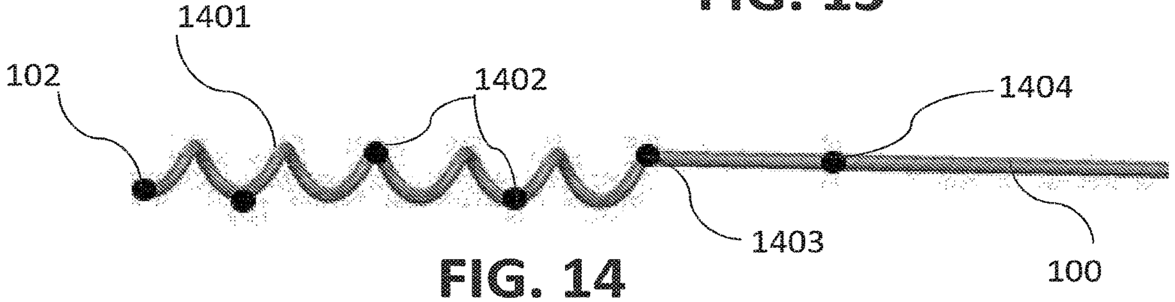
FIG. 14 is a side view of one embodiment in accordance with the present invention.

Referring to FIG. 14, an embodiment of guide wire 100 shows a helical shape 1401 with sensors 102, 1402, 1403, 1404 that could again yield information to the user as described above with respect to previous embodiments.

Figure 15:
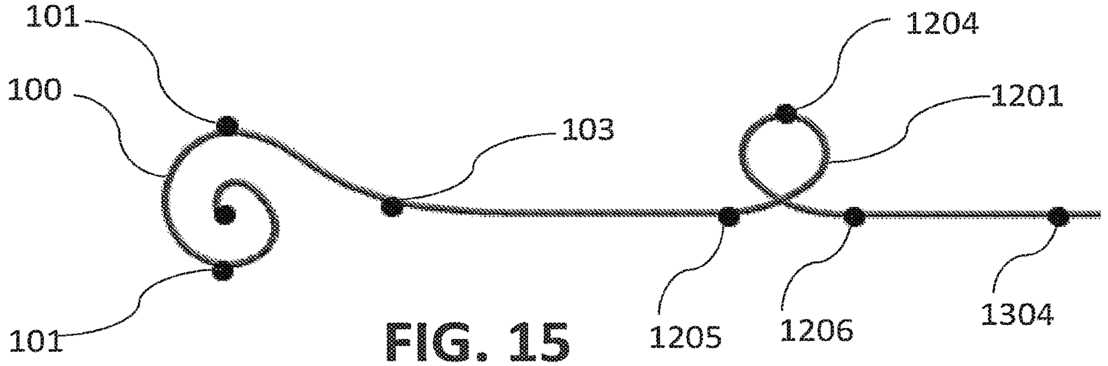
FIG. 15 is a side view of one embodiment in accordance with the present invention.

Referring to FIG. 15, an embodiment of guide wire 100 combines previously described features of the spiral member and a looped member 1201 with sensors 101, 103, 1205, 1204, 1206, 1304 that could again yield information to the user as described above with respect to previous embodiments.

Figure 16:
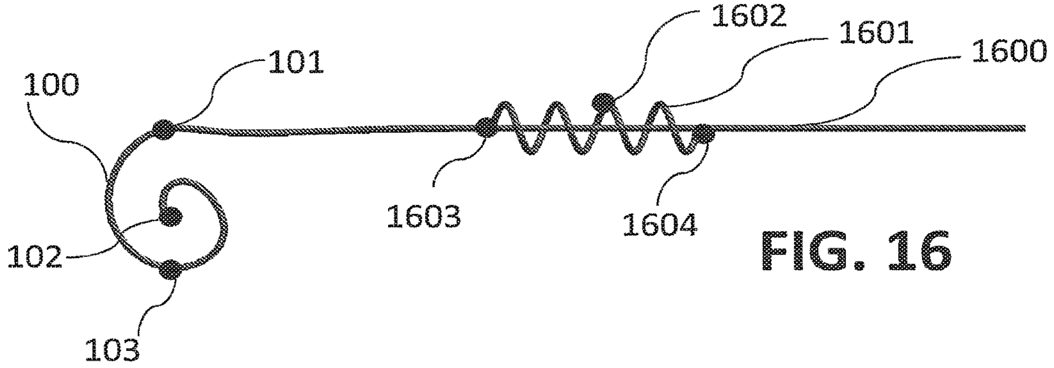
FIG. 16 is a side view of one embodiment in accordance with the present invention.

Referring to FIG. 16, an embodiment of guide wire 100 combines previously described features of the spiral member and the helical member 1601 with sensors 101, 102, 103, 1603, 1602, 1604 that could, again yield information to the user described above with respect to previous embodiments.

Referring to FIGS. 17-23, there are shown embodiments of a guide wire 100 with alternative expanding assembly configurations. It will be appreciated by one of skill in the art that components of previously described embodiments are usable with these embodiments as well.

Broadly speaking the embodiments of FIGS. 17-23 can employ multiple configurations, including nested members, an inner guidewire, expanding elements, an outer guide catheter or sheath, etc.

The expanding member can change in length during expansion and collapse with such changes correlating to changes in diameter of a vessel.

The shape of the expanding members can be virtually any expanding shape including helical coil, coil, loop, multiple loop, closed end coil, open ended coils, spirals, multiple spirals and the like.

The expandable members can be positioned on the wire of the guidewire or on a sheath member associated with the guide wire.

The shape of the expandable members could be any expanding shape including one deflecting member captured on one end, two or more deflecting members captured on one end, one deflecting member captured on two ends, two or more deflecting members captured on two ends, spiral deflecting members, helical deflecting members, cage like deflecting members, or combinations of any or all of these.

The expanding members can be made from braided material, extruded material, laser cut material, metal, plastic, or other. The construction could be a unitary member and assembly of different members. The relative position of the members can be measured internal to the anatomy as well as external to the body on the proximal end.

In another embodiment the guide wire has variable stiffness characteristics along its length. In one embodiment such stiffness is adjustable (along with adjustments in the length of stiffness segments) using techniques known to those of skill in the art.

In another embodiment, the guide wire 100 has a diameter that is adjustable along its length.

Such aforesaid attributes of a guide wire 100 are optimized to facilitate tactile feedback to the user, ensure the ability to advance the wire without prolapse, ensure that the intended trajectory is achieved, and provide external indication of the status or position of the apparatus.

In one embodiment, the guide wire 100 extends from the body or a guide catheter wherein the length of the extension dictates the stiffness of the device.

In another embodiment, the wire of the guide wire 100 could be made of a tapered core with a flexible outer feature like a coil. Such a design facilitates a flexible distal tip section with increased stiffness as the diameter of the tapered center increases.

In another embodiment, a catheter has multiple channels or large enough inner diameter to house two or more guidewire like elements such that the device increases in stiffness as multiple members are inserted into an outer catheter member.

In another embodiment, the wire is made from a coil with a pull wire in a middle core section. When tension is applied to the pull wire the entire device increases in stiffness because of the limited motion of adjacent coil members.

Other concepts are known in the art to introduce variable stiffness attributes to a guide wire. As will be appreciated by one of skill in the art, all embodiments disclosed herein which have multiple components will exhibit variations in stiffness during operation that enable use in accordance with the present invention.

Figure 17:
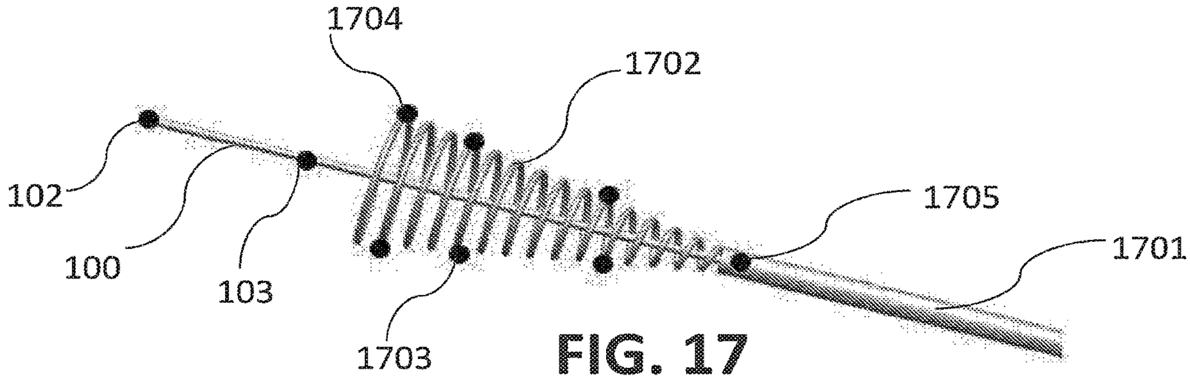
FIG. 17 is a side view of one embodiment in accordance with the present invention.

Referring to FIG. 17, an embodiment of guide wire 100 includes a tapered coil 1702 which is used to measure inductance change as an indicator of diameter change of a vessel. The guide wire 100 also includes sensors 102, 103, 1703, 1704, 1705.

As known in the art, the inductance of a coil is dependent on its geometry. As the tapered coil 1702 is passed through different vessel sizes, the shape of the coil 1702 similarly changes (compresses or lengthens). This shape change leads to an inductance change, which, accordingly, can be used to indicate position in a vessel.

Additionally, sensors 102, 103, 1703, 1704, 1705, are used, in the manner described above, to obtain conformational data to a change in geometry of the tapered coil 1702.

Figure 18:
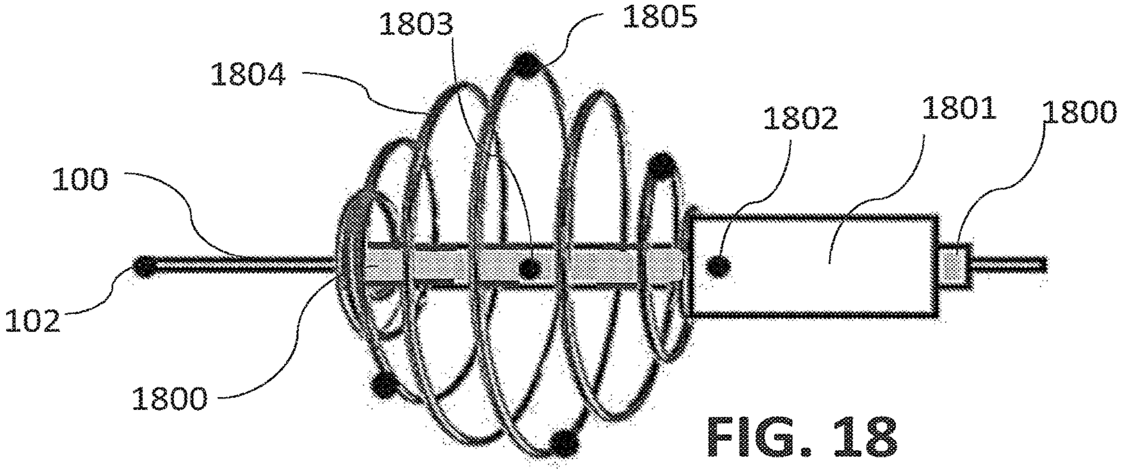
FIG. 18 is a side view of one embodiment in accordance with the present invention.

Referring to FIG. 18, an embodiment of guide wire 100 includes a oval or egg-shaped coil 1804 which is used to measure inductance change as an indicator of diameter change of a vessel. The guide wire 100 also includes sensors 102, 1802, 1803, and 1805.

As known in the art, the inductance of a coil is dependent on its geometry. As the oval or egg-shaped coil 1804 is passed through different vessel sizes, the shape of the coil 1804 similarly changes (compresses or lengthens). This shape change leads to an inductance change, which, accordingly, can be used to indicate position in a vessel.

Additionally, sensors 102, 1802, 1803, and 1805, are used, in the manner described above, to obtain conformational data to a change in geometry of the tapered coil 1804.

Figure 19:
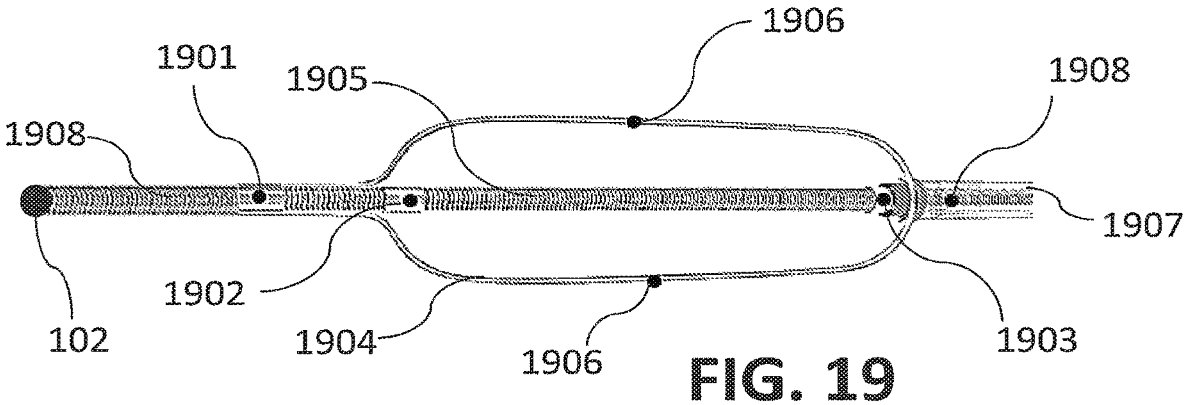
FIG. 19 is a side view of one embodiment in accordance with the present invention.

Referring to FIGS. 17-19, the guide wire 100 is independently movable relative to the expanding members 1702 and 1804.

Referring to FIG. 17, a guide sheath 1701 is also included.

Referring to FIG. 18, a guide wire 100 is surrounded by a first sheath 1800 and a second sheath 1802. Moreover, the distal end of the first sheath 1800 is attached to a distal end of expandable coil 1804. The distal end of second sheath 1802 is connected to the proximal end of expandable coil 1804. Guide wire 100 is freely axially movable relative to both sheaths 1800 and 1802. As will be appreciated by one of skill in the art, the concepts associated with the embodiment of FIG. 18 can be applied to all multi-component systems disclosed herein.

Referring to FIG. 19, an embodiment of a guide wire 100 includes an expandable wire member 1904 and having sensors 102, 1901, 1902, 1903, 1906 and 1908. This embodiment operates in a manner analogous to previously described embodiments which is equally applicable here. The expanding wire member 1904 is straight. The wire of the guide wire 100 can be a solid member or a wound cable of wires. The guide wire 100 can have multiple expandable members 1904 as will be appreciated by those of skill in the art. The guide wire 100 includes an outer member 1907 which can be an extruded tube, braided shaft or hollow stranded coil.

Figure 20:
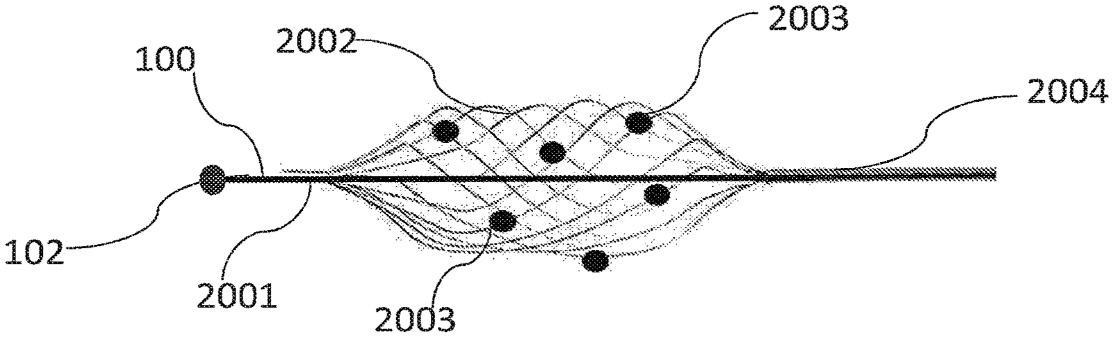
FIG. 20 is a side view of one embodiment in accordance with the present invention.

Referring to FIG. 20, an embodiment of a guide wire 100 includes an expandable member 2002 and having sensors 102, 2003. This embodiment operates in a manner analogous to previously described embodiments which is equally applicable here. The expanding member 2002 is helical. The wire of the guide wire 100 can be a solid member or a wound cable of wires. The guide wire 100 can have multiple expandable members 2002 as will be appreciated by those of skill in the art. This embodiment also includes a guide sheath 2004.

Figure 21:
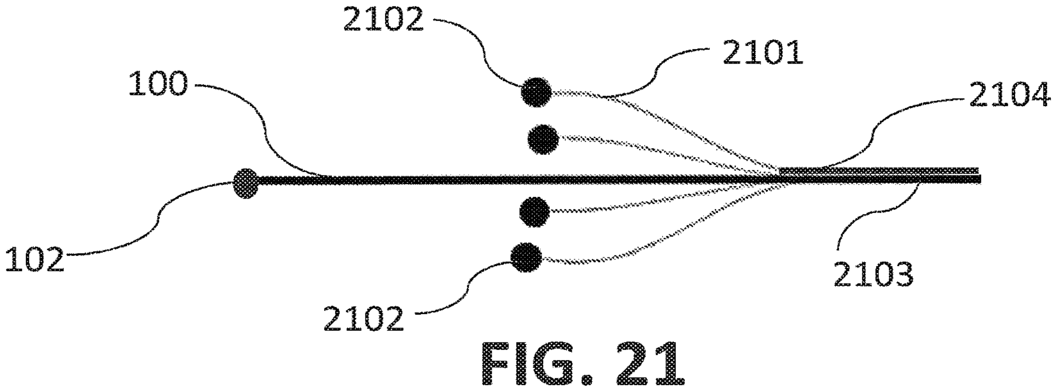
FIG. 21 is a side view of one embodiment in accordance with the present invention.

Referring to FIG. 21, an embodiment of a guide wire 100 includes expandable members 2101 constrained only on one end, for example by a guide sheath 2104 with sensors 2202 located on the free end of the expandable members 2101. An outer member 2103 is present in which the wire of guidewire 100 can freely pass.

Figure 22:
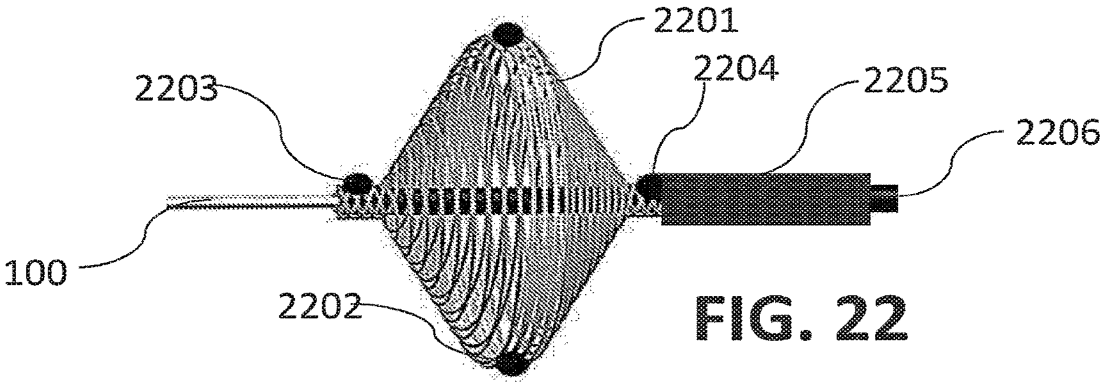
FIG. 22 is a side view of one embodiment in accordance with the present invention.

Referring to FIG. 22, an embodiment of a guide wire 100 includes an expandable member 2201 and having sensors 2202, 2203, 2204. This embodiment operates in a manner analogous to previously described embodiments which is equally applicable here. The expanding member 2201 is braided or coiled. The wire of the guide wire 100 can be a solid member or a wound cable of wires. The guide wire 100 can have multiple expandable members 2201 as will be appreciated by those of skill in the art. It also includes a sheath 2205 and an inner movable member 2206 connected to a distal end of the expanding member 2201.

Figure 23:
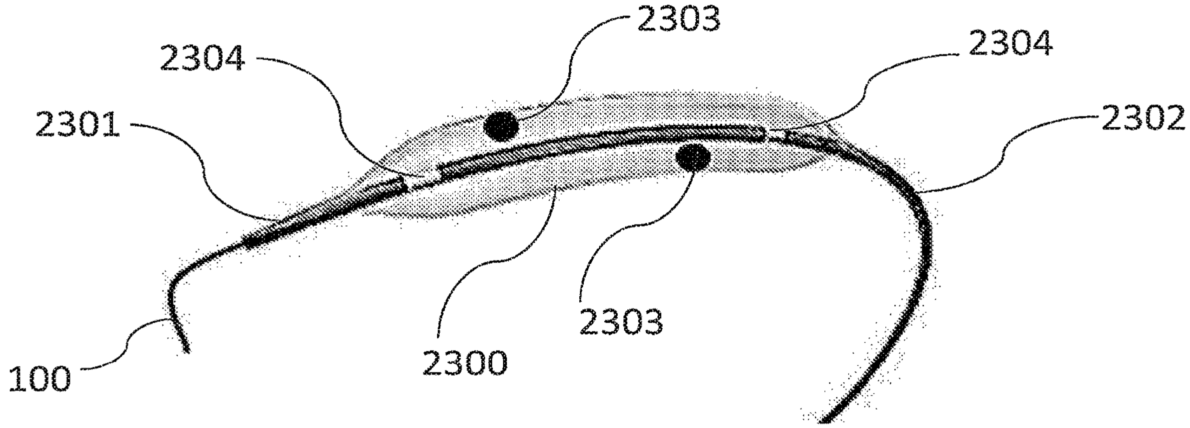
FIG. 23 is a side view of one embodiment in accordance with the present invention.

Referring to FIG. 23, an embodiment of guide wire 100 includes a balloon 2300 with integrated sensors 2303, 2304. The fluid used to fill the balloon is conductive. The amount of fluid in the balloon creates a varying electric field which is detectable and can be processed by external equipment 601 to calculate a size of the balloon, which, in turn can be correlated to vessel diameter. In one embodiment, the balloon 2300 is shaped to allow for passage of blood flow. This embodiment includes sheaths 2301, 2302 as known to those of skill in the art.

Figure 24:
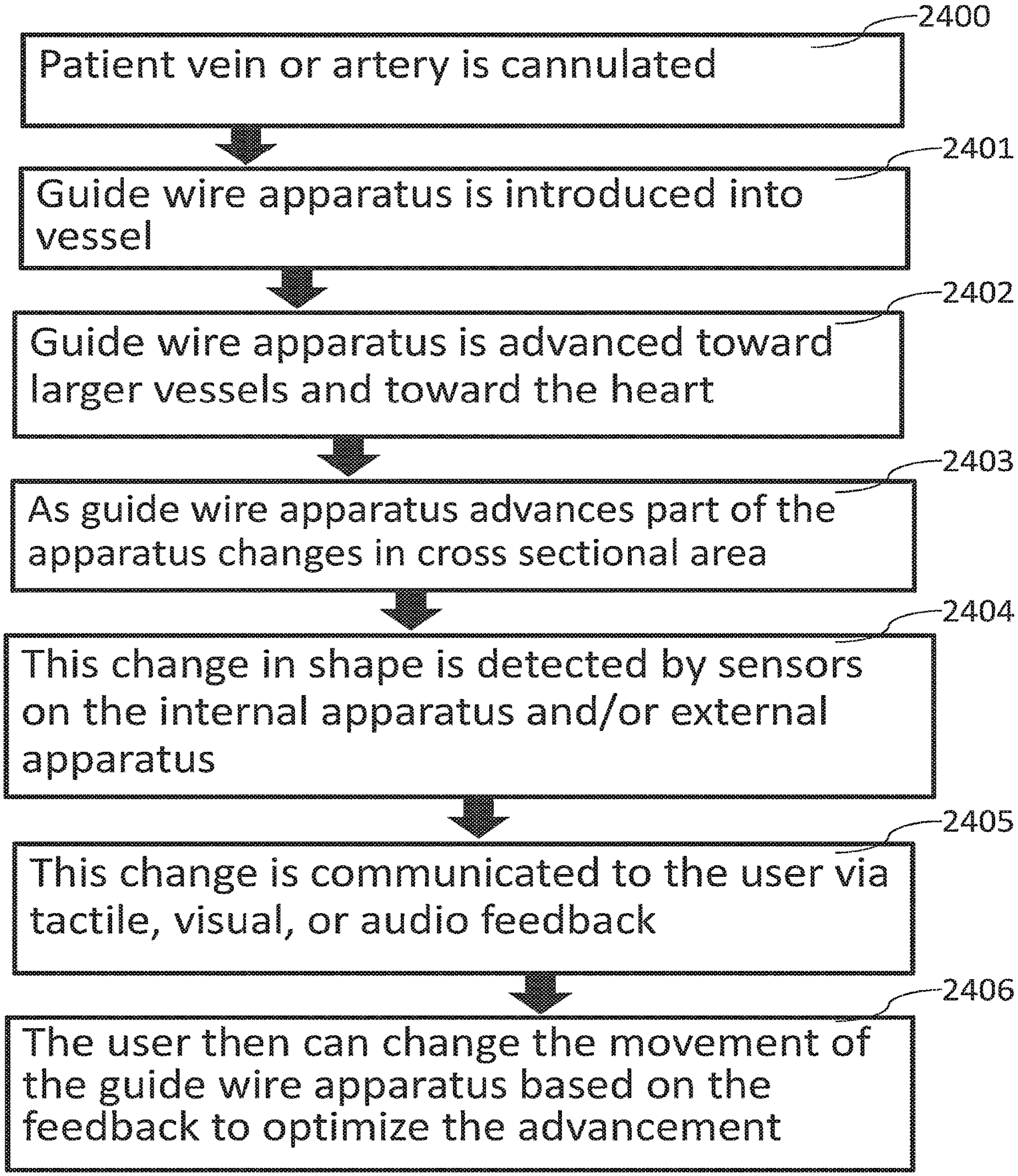
FIG. 24 is a block diagram showing an embodiment of a method in accordance with the present invention.

Referring to FIG. 24 a method in accordance with the present invention is depicted. First, a patient vein or artery is cannulated 2400 using standard vessel access techniques.

The guide wire apparatus is then introduced into the vessel through the cannulation 2401.

The guide wire apparatus is then advanced toward larger vessels, toward the heart 2402.

As the guide wire apparatus advances, cross-sectional areas of the vessels will change 2403, e.g., into vessels with smaller cross-sectional dimensions.

Changes in shape and cross-sectional dimensions is detected by sensors on the internal apparatus and/or external apparatus 2404. As will be appreciated by one of skill in the art, such detection can be performed by any of the aforementioned methods, e.g. resistance, magnetic, rf, tactile, pressure, etc.

This change in shape or cross-sectional dimension is sensed, processed and communicated to the user by, for example, tactile, visual, or audio feedback via an external equipment that works with the sensors and guidewire apparatus 2405.

The user then changes, if necessary, the movement of the guide wire apparatus based on the feedback to optimize the advancement 2406. Such changes can include retraction of the device, rotation of the device, steering of the device, readvancement of the device, or other motion that facilitates the desired advancement to the desired location in the body. There are many combinations of expansion, deflection, constriction, bending and the like that can happen and those all could be communicated to the user.

The trajectory of the guidewire apparatus could have many multiple obstructions, tortuosity, alternate vessel paths each of which to be sensed by the sensors on the apparatus. These trajectories and combinations are sensed by, for example, the multiple modalities listed herein and measured and/or calculated to an external equipment. The equipment then communicates this information to the user via, for example, haptic feedback, lights, sound, visual displays, and the like.

As used herein, the terms "substantially" or "generally" refer to the complete or nearly complete extent or degree of an action, characteristic, property, state, structure, item, or result.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Still further, the figures depict preferred embodiments for purposes of illustration only. One skilled in the art will readily recognize from the discussion herein that alternative embodiments of the structures and methods illustrated herein may be employed without departing from the principles described herein.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention. Any feature of any embodiment described herein may be used in any embodiment and with any features of any other embodiment.

What is claimed is:

1. A method for percutaneously positioning a medical device within a vasculature of a patient, the method comprising:

inserting a distal region of the medical device into a first vasculature region of the patient having a first cross-sectional dimension, wherein the distal region of the medical device includes a flexible mechanism having a plurality of positional elements, wherein the flexible mechanism is configured to reversibly transition between a first configuration and a second configuration, and wherein, when in the first vasculature region, the flexible mechanism is in the first configuration;

advancing the distal region of the medical device from the first vasculature region to a second vasculature region of the patient, wherein the second vasculature region includes a second cross-sectional dimension different from the first cross-sectional dimension, and wherein, when in the second vasculature region, the flexible mechanism transitions to the second configuration;

determining a change in a distance between a first positional element and a second positional element of the plurality of positional elements; and correlating the determined change in distance to a change in cross-sectional dimension of the vasculature.

2. The method of claim 1, wherein the method is performed without using adjunctive imaging tools.

3. The method of claim 1, wherein the method is performed without using fluoroscopy.

4. The method of claim 1, further comprising:

adjusting a position of the flexible mechanism based on the determined change in the distance between the first positional element and the second positional element.

5. The method of claim 1, further comprising:

retracting the distal region of the medical device from the second vasculature region to the first vasculature region when the distance between the first positional element and the second positional element decreases.

6. The method of claim 5, further comprising:

re-advancing the distal region of the medical device from the first vasculature region and towards a desired location of the vasculature.

7. The method of claim 1, wherein the plurality of positional elements includes sensors operably coupled to equipment located externally of the patient.

8. The method of claim 1, wherein the change in the distance between the first positional element and the second positional element is determined by a processor located externally of the patient.

9. The method of claim 1, wherein the first configuration is an expanded configuration, and wherein the second configuration is a further expanded configuration.

10. The method of claim 1, wherein the first configuration is an expanded configuration, and wherein the second configuration is a contracted configuration.

11. The method of claim 1, wherein the vasculature of the patient includes one of a femoral vein or artery.

12. The method of claim 1, further comprising:
- advancing the distal region of the medical device from the second vasculature region to a third vasculature region when the distance between the first positional element and the second positional element increases.

13. The method of claim 1, wherein the method includes extracorporeal membrane oxygen (ECMO) support.

14. The method of claim 1, wherein the method is performed outside of an imaging suite or a hospital.

15. A method for positioning a guide wire within a vasculature of a patient, the method comprising:
- cannulating a blood vessel of the patient;
- introducing the guide wire into a first region of the blood vessel, wherein the first region of the blood vessel has a first cross-sectional dimension, wherein a distal region of the guide wire includes a flexible mechanism configured to reversibly transition between a first configuration and a second configuration, wherein the flexible mechanism includes a plurality of positional elements, and wherein, when in the first region of the blood vessel, the flexible mechanism is in the first configuration;
- advancing the guide wire from the first region of the blood vessel to a second region of the blood vessel, wherein the second region of the blood vessel has a second cross-sectional dimension larger than the first cross-sectional dimension, and wherein, when in the second region, the flexible mechanism transitions to the second configuration;
- determining a change in a distance between a first positional element and a second positional element of the plurality of positional elements;
- correlating the determined change in distance to a change in cross-sectional dimension of the vasculature; and
- generating an indication of the correlated change in cross-sectional dimension of the vasculature by one of a tactile, visual, or audio feedback.

16. The method of claim 15, wherein the plurality of positional elements are sensors operably coupled to equipment located externally of the patient.

17. The method of claim 15, further comprising manipulating the guide wire to adjust a location of the flexible mechanism.

18. A system for positioning a guide wire within a vasculature of a patient the system comprising:
- a guide wire having a distal region, wherein the distal region includes an expandable flexible mechanism, wherein the expandable flexible mechanism includes a plurality of positional elements configured to generate information correlating to spatial positioning of each of the plurality of positional elements relative to one another when the expandable flexible mechanism is positioned within the vasculature of the patient; and
- external equipment configured for receiving the information generated by the plurality of positional elements, wherein the external equipment further includes a processor configured to execute code to determine a change in distance between any two positional elements of the plurality of positional elements, wherein the processor is further configured to determine a cross-sectional dimension of the vasculature of the patient from spatial positioning of each of the plurality of positional elements relative to one another, and wherein the system is configured to position the guide wire within the vasculature of the patient without using imaging guidance.

19. The system of claim 18, wherein the information is received wirelessly by the external equipment.

20. The system of claim 18, wherein the processor is further configured to determine a cross-sectional dimension of the expandable flexible mechanism from spatial positioning of each of the plurality of positional elements relative to one another.

21. The system of claim 18, wherein the system is configured to position the guide wire without the use of adjunctive imaging tools, and wherein the system is configured to position the guide wire without the use of any previously acquired images from adjunctive imaging tools.

* * * * *